United States Patent
Cartier-Lacave et al.

(10) Patent No.: US 10,159,227 B2
(45) Date of Patent: Dec. 25, 2018

(54) ALZHEIMER'S DISEASE ANIMAL MODEL

(71) Applicants: INSERM (Institut National de la Sante et de la Recherche Medicale), Paris (FR); Universite de Paris—Sud, Orsay (FR); Commissariat a l'Energie Atomique et aux Energies Alternatives, Paris (FR); Centre National de la Recherche Scientifique (CNRS), Paris (FR); Universite Paris Descartes, Paris (FR)

(72) Inventors: Nathalie Cartier-Lacave, Le Kremlin Bicetre (FR); Jerome Braudeau, Le Kremlin Bicetre (FR); Nicole Deglon, Fontenay-aux-Roses (FR); Philippe Hantraye, Fontenay-aux Roses (FR); Mickael Audrain, Le Kremlin Bicetre (FR)

(73) Assignees: INSERM (Institut National de la Sante et de la Recherche Medicale), Paris (FR); Universite de Paris—Sud, Orsay (FR); Commissariat a l'Energie Atomique et aux Energies Alternatives, Paris (FR); Centre National de la Recherche Scientifique (CNRS), Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 15/034,370

(22) PCT Filed: Nov. 5, 2014

(86) PCT No.: PCT/EP2014/073838
§ 371 (c)(1),
(2) Date: May 4, 2016

(87) PCT Pub. No.: WO2015/067668
PCT Pub. Date: May 14, 2015

(65) Prior Publication Data
US 2016/0262361 A1      Sep. 15, 2016

(30) Foreign Application Priority Data

Nov. 5, 2013 (EP) .................... 13306518

(51) Int. Cl.
| | |
|---|---|
| *A01K 67/00* | (2006.01) |
| *A01K 67/033* | (2006.01) |
| *A01K 67/027* | (2006.01) |
| *C12N 15/85* | (2006.01) |
| *C12N 15/86* | (2006.01) |
| *G01N 33/50* | (2006.01) |
| *C07K 14/47* | (2006.01) |

(52) U.S. Cl.
CPC ...... *A01K 67/0278* (2013.01); *C12N 15/8509* (2013.01); *C12N 15/86* (2013.01); *G01N 33/5088* (2013.01); *A01K 2207/15* (2013.01); *A01K 2217/00* (2013.01); *A01K 2217/05* (2013.01); *A01K 2217/052* (2013.01); *A01K 2227/105* (2013.01); *A01K 2267/03* (2013.01); *A01K 2267/0312* (2013.01); *A01K 2267/0318* (2013.01); *C07K 14/4711* (2013.01); *C12N 2015/8545* (2013.01); *C12N 2750/14143* (2013.01); *G01N 2333/47* (2013.01)

(58) Field of Classification Search
CPC ................... C12N 2015/8545; C12N 15/8509
USPC .............................................. 800/18, 12, 23
See application file for complete search history.

(56) References Cited

FOREIGN PATENT DOCUMENTS

| WO | 01/20977 A1 | 3/2001 |
|---|---|---|
| WO | 02/063951 A2 | 8/2002 |
| WO | 2012/049314 A1 | 4/2012 |

OTHER PUBLICATIONS

Wirths, 2006, Acta Neuropathol, 111:312-319.*
Rodriguez-Vieitez, 2015, Eur J Med Mol Imaging, 42:1119-1132.*
Dayton, 2012, Expert Opinion on Biological Therapy, 12:757-766.*
Jankowsky, 2004, Human Molecular Genetics, 13:159-170.*
Cedarfjall, 2012, Molecular Therapy, 20:1315-1326.*
Jankowsky et al.; "Co-expression of multiple transgenes in mouse CNS: a comparison of strategies"; Biomolecular Engineering, vol. 17, No. 6, 2001-06, pp. 157-165.
Cacquevel et al.; "Modelling Alzheimer's Disease Through Adeno-Associated Virus (AAV) Vector Gene Delivery in the Mouse Brain"; Alzheimer's & Dementia, vol. 7, No. 4, Jul. 2011, pp. S121-S122.
Guo et al.; "APP physiological and pathophysiological functions: insights from animal models"; Cell Research, vol. 22, No. 1, Jul. 19, 2011, pp. 78-89.
Blanchard et al.; "Time sequence of maturation of dystrophic neurites associated with Abeta deposits in APP/PS1 transgenic mice"; Experimental Neurology, vol. 184, No. 1, Nov. 2003, pp. 247-263.

(Continued)

*Primary Examiner* — Valarie E Bertoglio
(74) *Attorney, Agent, or Firm* — Whitham & Cook, P.C.

(57) ABSTRACT

The present invention relates to a vector comprising a nucleic acid sequence that encodes the APP protein and/or the PS1 protein or variants thereof. The invention also relates to a method for inducing the Alzheimer's disease in an animal using the vector of the invention and to animal model having the Alzheimer's disease obtained by said method.

12 Claims, 11 Drawing Sheets
Specification includes a Sequence Listing.

(56) References Cited

OTHER PUBLICATIONS

Klein et al.; "AAV8, 9, Rh10, Rh43 Vector Gene Transfer in the Rat Brain: Effects of Serotype, Promoter and Purification Method"; Molecular Therapy, vol. 16, No. 1, Oct. 23, 2007, pp. 89-96.
Peel et al.; "Adeno-associated virus vectors: activity and applications in the CNS"; Journal of Neuroscience Methods, vol. 98, No. 2, Jun. 2000, pp. 95-104.

* cited by examiner

Figure 6:
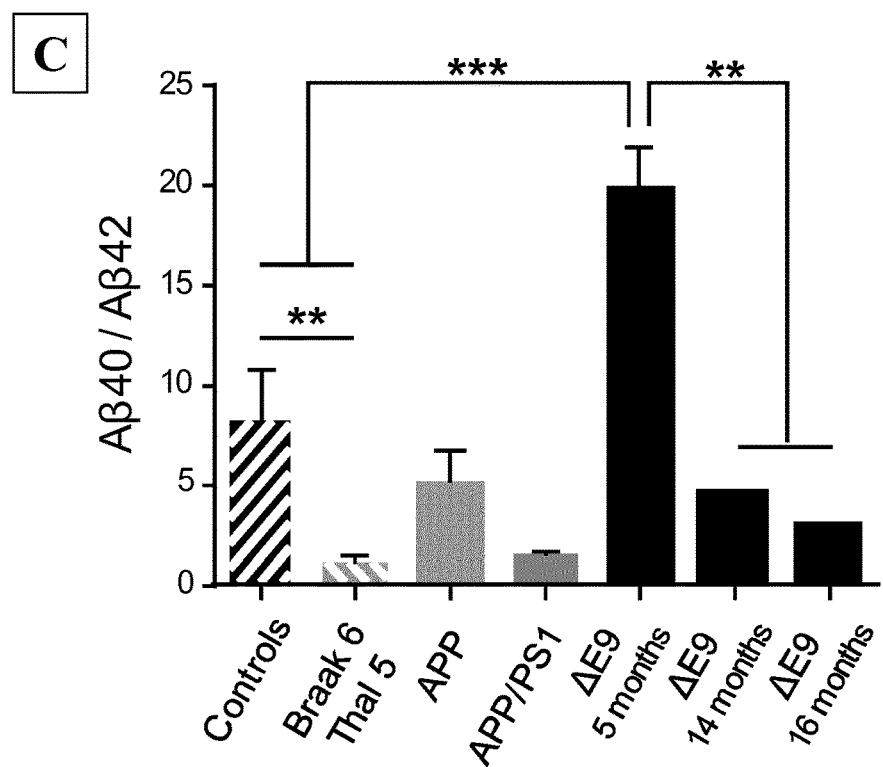

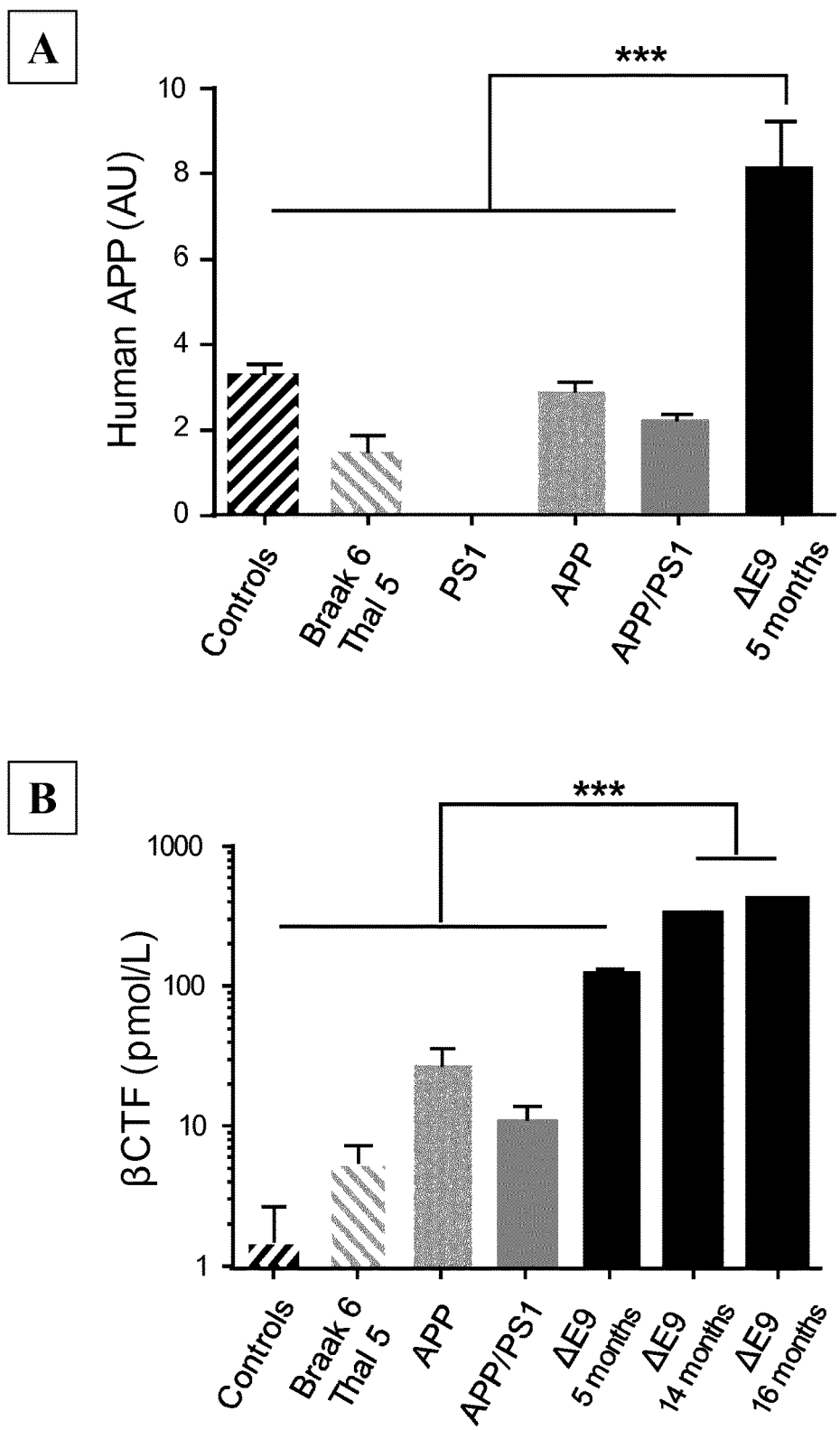
Figure 6 A and B

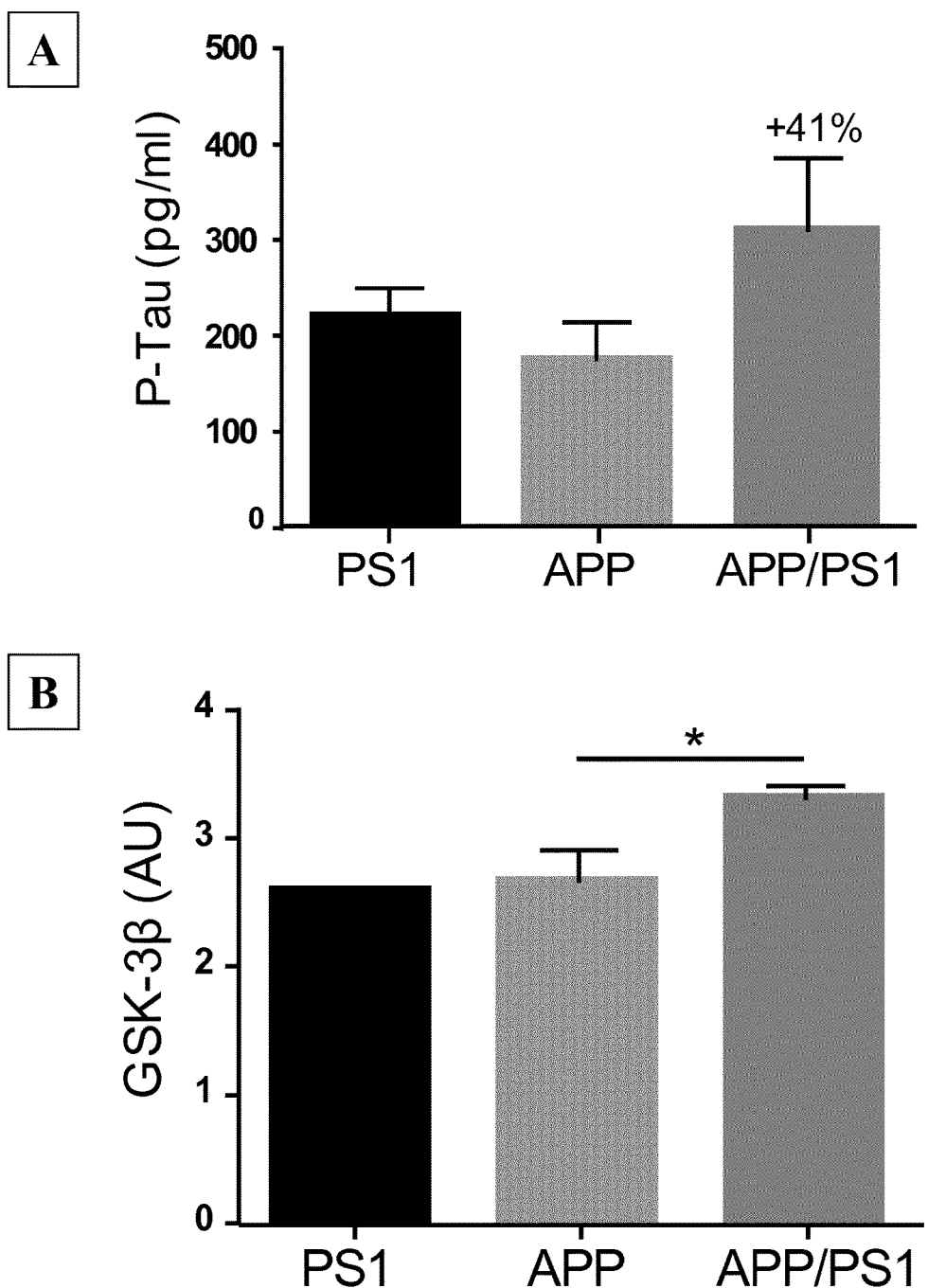
Figure 7 A and B

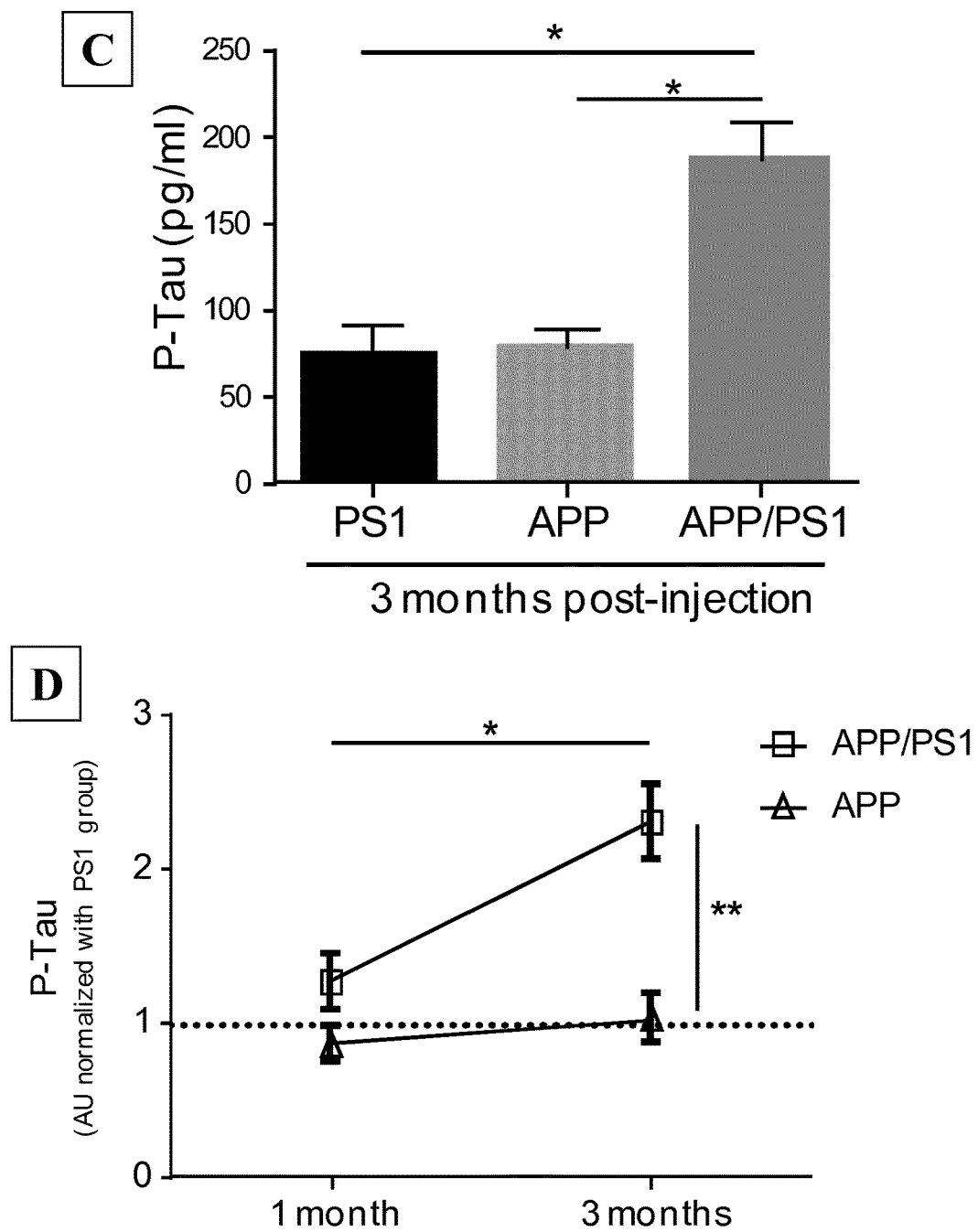
Figure 7 C and D

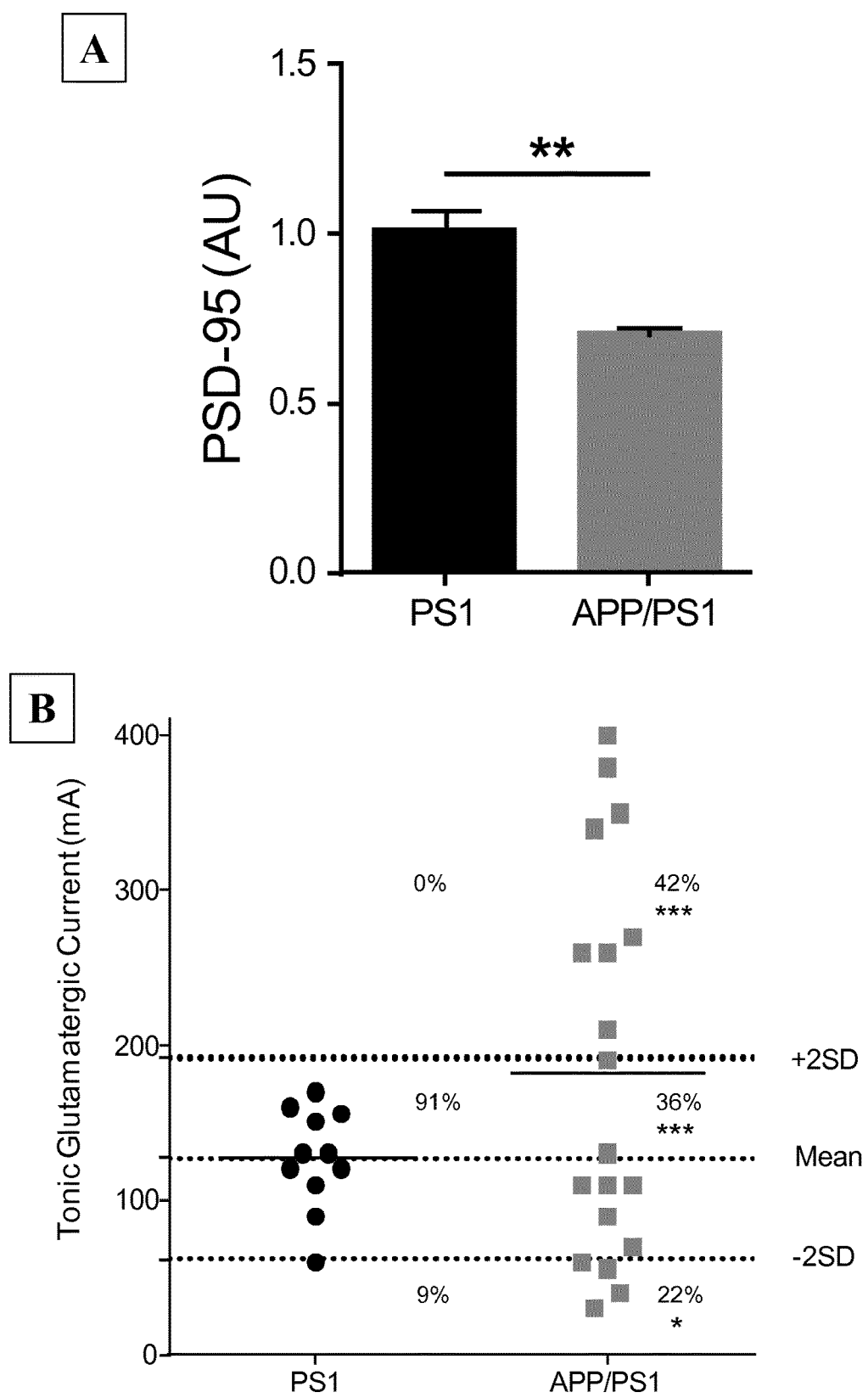
Figure 8 A and B

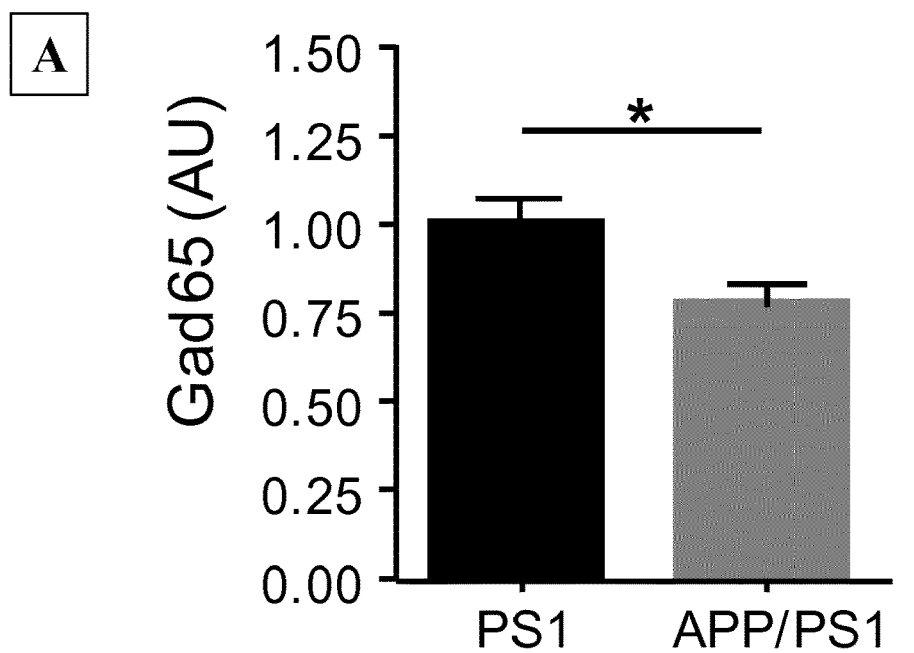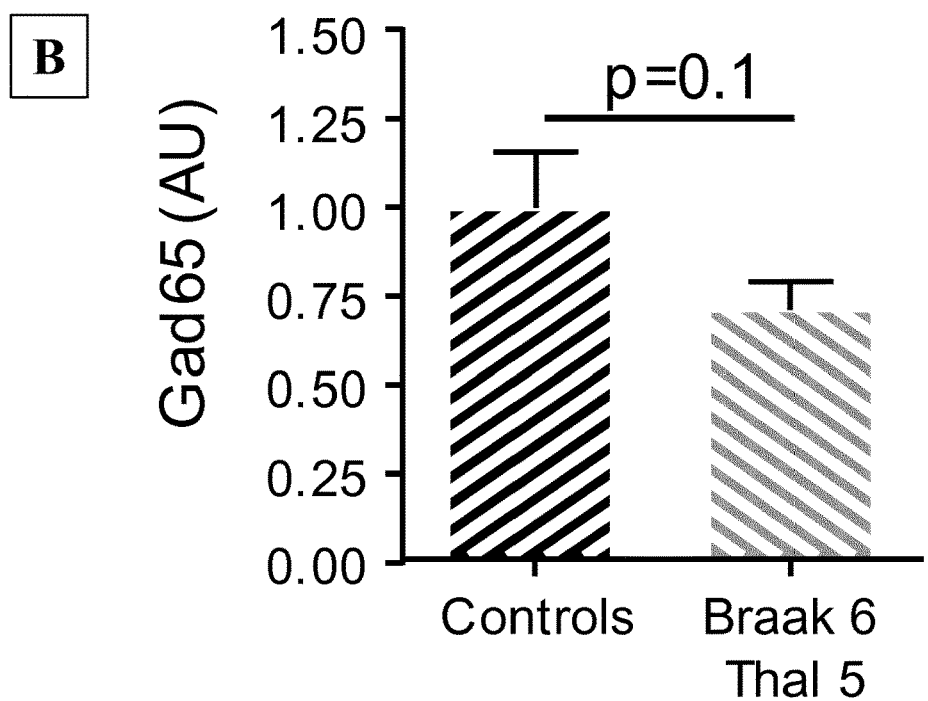
Figure 9 A and B

ALZHEIMER'S DISEASE ANIMAL MODEL

FIELD OF THE INVENTION

The present invention relates to a vector comprising a nucleic acid sequence that encodes the APP protein and/or the PS1 protein or variants thereof.

The invention also relates to a method for inducing Alzheimer's disease in an animal using the vector of the invention and to animal model having Alzheimer's disease obtained by said method.

BACKGROUND OF THE INVENTION

Alzheimer's disease (AD) is the most frequently encountered form of dementia (about 70% of dementia cases). With improved life expectancy, especially in developed countries, the incidence of dementia has dramatically increased and current forecasts speak in terms of a doubling of the number of persons affected every 20 years. In France, it is estimated that more than 850,000 people (with a majority of woman) are currently suffering from dementia, and around 225,000 new cases appear each year. AD is characterized by the accumulation of senile plaques (SP), neurofibrillary tangles (NFT), and selective synaptic and neuronal loss in plaques are composed of insoluble extracellular aggregates consisting mainly of amyloid β (Aβ) peptides derived from proteolytic cleavages of the amyloid precursor protein (APP). Genetic studies, together with the demonstration of a direct toxic effect of Aβ, led to the development of the amyloid cascade hypothesis to explain the Aβ-associated neurodegenerative process. Aβ rapidly aggregates to form amorphous and fibrillar oligomers, which then deposit to build senile plaques. A number of studies have provided evidence that βCTF and soluble Aβ oligomers are more toxic to cells than mature fibrils (Kayed et al., 2003) and these neurotoxic peptides are originally produced by the cleavage of APP.

Mutations in genes that encode APP or proteases that generate Aβ (PS1; PS2) are responsible for the familial forms (5% of cases) of AD (Selkoe et al., 2001).

Different AD animal models have been developed, most of them being transgenic mouse models obtained by transferring genes carrying mutations identified in familial AD including APP, PS1 and PS2 (Lee and Han, 2013). Although not perfect, these models offer a mean to gain knowledge on the physiopathology of AD but they also suffer from various limitations (expression of neurotoxic peptides from in utero development, associated compensatory effect, genetic drift in particular) which impair their use in research.

The use of viral vectors to develop experimental models would be a valuable breakthrough in the field. AAV vectors are attractive tools for gene transfer in the central nervous system (CNS) due to their lack of toxicity, their strong capacity to transduce neurons and to stably express recombinant proteins (for several years in rodents, dogs and primates). Viral vectors have already and are currently being used in several clinical trials in human patients worldwide (Cartier et al., 2009). The use of viral vectors to develop new animal models of neurodegenerative disorders is currently under investigation (Deglon and Hantraye, 2005). This strategy holds various advantages compared to classical transgenic approaches: viral vectors are versatile, highly flexible tools to perform in vivo studies and multiple genetic models can be created in a short period of time. High transduction efficiencies as well as robust and sustained transgene expression lead to the rapid appearance of functional and behavioral abnormalities and severe neurodegeneration. Targeted injections in different brain areas can be used to investigate the regional specificity of the neuropathology and eliminate potential side effects associated with a widespread overexpression of the transgene. Finally, models can be established in different mammalian species including large animals like dogs, pigs and non-human primates, thereby providing an opportunity to assess complex behavioral changes and perform longitudinal follow-up of neuropathological alterations by imaging. Lentiviral or AAV vectors were successfully injected in the brain of adult mice, rats or primates to create models of various neurodegenerative diseases such as Huntington's, Parkinson's, Machado-Joseph diseases (Kirik et al., 2002; Lo Bianco et al., 2002).

SUMMARY OF THE INVENTION

The inventors have now developed an efficient and powerful animal model of Alzheimer's disease by using optimized APPsl and PS1 genes and Adeno-associated virus (AAV) vectors.

Thus, the invention relates to a vector comprising a nucleic acid sequence that encodes the APP protein and/or the PS1 protein or variants thereof.

The invention also relates to a method for inducing the Alzheimer's disease in an animal using the vector of the invention and to animal model having the Alzheimer's disease obtained by said method.

DETAILED DESCRIPTION OF THE INVENTION

Vectors of the Invention

A first object of the invention relates to a vector comprising a nucleic acid sequence that encodes the APP protein and/or the PS1 protein or variants thereof.

In one embodiment, the vector of the invention comprises a nucleic acid sequence that encodes the APP protein and a nucleic acid sequence that encodes the PS1 protein.

In another embodiment, the vector of the invention may comprises any variant of the nucleic acid sequence which encodes for the APP protein and/or any variant of the nucleic acid sequence which encodes for the PS1 protein.

In another embodiment, the vector of the invention may comprises any variant of the nucleic acid sequence which encodes for any variant of the APP protein and/or any variant of the nucleic acid sequence which encodes for any variant of the PS1 protein.

In another embodiment, the invention relates to a vector comprising a nucleic acid sequence that encodes the APP protein or variants thereof and a vector comprising a nucleic acid sequence that encodes the PS1 protein or variants thereof.

As used herein, the term "APP" or "Amyloid Precursor Protein" denotes an integral membrane protein expressed in many tissues and concentrated in the synapses of neurons. Its primary function is not known, though it has been implicated as a regulator of synapse formation, neural plasticity and iron export. APP is best known as the precursor molecule whose proteolysis generates beta amyloid (Aβ), a 37 to 49 amino acid peptide whose amyloid fibrillar form is the primary component of amyloid plaques found in the brains of Alzheimer's disease patients. The cDNA sequence for APP is disclosed in Genbank under access number Gene ID: 351 and has the sequence SEQ ID NO:1 as described below:

ATGCTGCCCGGACTGGCTCTGCTGCTGCTGGCCGCTTGGACCGCCAGAGC

CCTGGAAGTGCCCACCGATGGCAATGCTGGCCTGCTGGCCGAGCCCCAGA

TCGCCATGTTCTGCGGCAGACTGAACATGCACATGAACGTGCAGAACGGC

AAGTGGGACAGCGACCCCAGCGGCACCAAGACCTGCATCGACACCAAAGA

GGGCATCCTGCAGTATTGCCAGGAAGTGTACCCCGAGCTGCAGATCACCA

ACGTGGTGGAAGCCAACCAGCCCGTGACCATCCAGAACTGGTGCAAGCGG

GGCAGAAAGCAGTGCAAGACCCACCCCCACTTCGTGATCCCTTACCGGTG

CCTGGTCGGAGAGTTCGTGTCCGACGCCCTGCTGGTGCCCGACAAGTGCA

AGTTCCTGCATCAGGAACGGATGGACGTCTGCGAGACACATCTGCACTGG

CACACCGTGGCCAAAGAGACATGCAGCGAGAAGTCCACCAACCTGCACGA

CTACGGCATGCTGCTGCCCTGCGGCATCGACAAGTTCCGGGGCGTGGAAT

TCGTGTGCTGCCCCCTGGCCGAGGAATCCGACAACGTGGACAGCGCCGAC

GCCGAAGAGGACGACAGCGACGTGTGGTGGGGCGGAGCCGACACCGATTA

CGCCGACGGCAGCGAGGACAAGGTCGTGGAAGTGGCTGAAGAGGAAGAGG

TGGCCGAGGTCGAAGAAGAGGAAGCCGACGACGACGAGGATGACGAGGAC

GGCGACGAAGTGGAAGAAGAAGCCGAGGAACCCTACGAGGAAGCCACCGA

GCGGACCACCTCTATCGCCACCACCACCACAACCACTACCGAGAGCGTGG

AAGAGGTGGTGCGCGAAGTGTGCAGCGAGCAGGCCGAGACAGGCCCCTGC

CGGGCCATGATCAGCCGGTGGTACTTCGACGTGACCGAGGGCAAGTGCGC

CCCCTTCTTCTATGGCGGCTGCGGCGGCAACCGGAACAACTTCGACACCG

AGGAATACTGCATGGCCGTGTGCGGCAGCGCCATCCCTACCACAGCCGCC

AGCACCCCCGACGCCGTGGACAAGTACCTGGAAACCCCTGGCGACGAGAA

CGAGCACGCCCACTTCCAGAAGGCCAAAGAGCGGCTGGAAGCCAAGCACC

GCGAGCGGATGAGCCAGGTGATGAGAGAGTGGGAAGAGGCCGAGAGACAG

GCCAAGAACCTGCCCAAGGCCGACAAGAAAGCCGTGATCCAGCACTTCCA

GGAAAAGGTCGAAAGCCTGGAACAGGAAGCCGCCAACGAGCGGCAGCAGC

TGGTGGAAACCCACATGGCCAGAGTGGAAGCCATGCTGAACGACCGGCGG

AGACTGGCCCTGGAAAACTACATCACCGCCCTGCAGGCCGTGCCCCCCAG

ACCCAGACACGTGTTCAACATGCTGAAGAAATACGTGCGGGCCGAGCAGA

AGGACCGGCAGCACACCCTGAAGCACTTCGAGCACGTGCGGATGGTGGAC

CCCAAGAAGGCCGCCCAGATCCGCTCTCAGGTCATGACCCACCTGAGAGT

GATCTACGAGAGAATGAACCAGAGCCTGAGCCTGCTGTACAATGTGCCCG

CCGTGGCCGAAGAAATCCAGGACGAGGTGGACGAGCTGCTGCAGAAAGAG

CAGAACTACAGCGACGACGTGCTGGCCAACATGATCAGCGAGCCCCGGAT

CAGCTACGGCAACGACGCCCTGATGCCCAGCCTGACCGAGACAAAGACCA

CCGTGGAACTGCTGCCCGTGAACGGCGAGTTCAGCCTGGACGACCTGCAG

CCCTGGCACAGCTTTGGCGCTGATAGCGTGCCCGCCAACACCGAGAACGA

GGTGGAACCCGTGGACGCCAGACCTGCCGCCGACAGAGGCCTGACCACAA

GACCTGGCAGCGGCCTGACCAACATCAAGACCGAAGAGATCAGCGAAGTG

AACCTGGACGCCGAGTTCCGGCACGACAGCGGCTACGAGGTGCACCACCA

GAAACTGGTGTTCTTCGCCGAGGACGTGGGCAGCAACAAGGGCGCCATCA

TCGGCCTGATGGTCGGAGGCGTGGTGATCGCCACCGTGATCATCATCACC

CTGGTGATGCTGAAAAAGAAGCAGTACACCAGCATCCACCACGGCGTGGT

CGAAGTGGACGCCGCTGTGACCCCCGAGGAACGGCACCTGAGCAAGATGC

AGCAGAACGGCTACGAGAACCCCACCTACAAGTTCTTCGAGCAGATGCAG

AACTGA.

The protein sequence of the APP protein has the sequence SEQ ID NO: 2 as described below:

MLPGLALLLLAAWTARALEVPTDGNAGLLAEPQIAMFCGRLNMHMNVQNG

KWDSDPSGTKTCIDTKEGILQYCQEVYPELQITNVVEANQPVTIQNWCKR

GRKQCKTHPHFVIPYRCLVGEFVSDALLVPDKCKFLHQERMDVCETHLHW

HTVAKETCSEKSTNLHDYGMLLPCGIDKFRGVEFVCCPLAEESDNVDSAD

AEEDDSDVWWGGADTDYADGSEDKVVEVAEEEEVAEVEEEEADDDEDDED

GDEVEEEAEEPYEEATERTTSIATTTTTTTESVEEVVREVCSEQAETGPC

RAMISRWYFDVTEGKCAPFFYGGCGGNRNNFDTEEYCMAVCGSAIPTTAA

STPDAVDKYLETPGDENEHAHFQKAKERLEAKHRERMSQVMREWEEAERQ

AKNLPKADKKAVIQHFQEKVESLEQEAANERQQLVETHMARVEAMLNDRR

RLALENYITALQAVPPRPRHVFNMLKKYVRAEQKDRQHTLKHFEHVRMVD

PKKAAQIRSQVMTHLRVIYERMNQSLSLLYNVPAVAEEIQDEVDELLQKE

QNYSDDVLANMISEPRISYGNDALMPSLTETKTTVELLPVNGEFSLDDLQ

PWHSFGADSVPANTENEVEPVDARPAADRGLTTRPGSGLTNIKTEEISEV

NLDAEFRHDSGYEVHHQKLVFFAEDVGSNKGAIIGLMVGGVVIATVIIIT

LVMLKKKQYTSIHHGVVEVDAAVTPEERHLSKMQQNGYENPTYKFFEQMQ

N.

In another embodiment, the APP used according to the invention is the APP (SEQ ID NO: 2) with the Swedish and London mutations (APPsl) which has the following protein sequence (SEQ ID NO: 3):

MLPGLALLLLAAWTARALEVPTDGNAGLLAEPQIAMFCGRLNMHMNVQNG

KWDSDPSGTKTCIDTKEGILQYCQEVYPELQITNVVEANQPVTIQNWCKR

GRKQCKTHPHFVIPYRCLVGEFVSDALLVPDKCKFLHQERMDVCETHLHW

HTVAKETCSEKSTNLHDYGMLLPCGIDKFRGVEFVCCPLAEESDNVDSAD

AEEDDSDVWWGGADTDYADGSEDKVVEVAEEEEVAEVEEEEADDDEDDED

GDEVEEEAEEPYEEATERTTSIATTTTTTTESVEEVVREVCSEQAETGPC

RAMISRWYFDVTEGKCAPFFYGGCGGNRNNFDTEEYCMAVCGSAIPTTAA

STPDAVDKYLETPGDENEHAHFQKAKERLEAKHRERMSQVMREWEEAERQ

AKNLPKADKKAVIQHFQEKVESLEQEAANERQQLVETHMARVEAMLNDRR

RLALENYITALQAVPPRPRHVFNMLKKYVRAEQKDRQHTLKHFEHVRMVD

PKKAAQIRSQVMTHLRVIYERMNQSLSLLYNVPAVAEEIQDEVDELLQKE

QNYSDDVLANMISEPRISYGNDALMPSLTETKTTVELLPVNGEFSLDDLQ

PWHSFGADSVPANTENEVEPVDARPAADRGLTTRPGSGLTNIKTEEISEV

-continued

```
KMDAEFRHDSGYEVHHQKLVFFAEDVGSNKGAIIGLMVGGVVIATVIVIT

LVMLKKKQYTSIHHGVVEVDAAVTPEERHLSKMQQNGYENPTYKFFEQMQ

N.
```

As used herein, the term "PS1" or "Presenilin 1" denotes a protein encoded by the PSEN1 gene. Presenilin 1 is one of the four core proteins in presenilin complex, which mediate the regulated proteolytic events of several proteins in the cell, including gamma secretase. Gamma-secretase is considered to play a strong role in generation of beta amyloid, accumulation of which is related to the onset of Alzheimer's disease, from the beta-amyloid precursor protein. The cDNA sequence for PS1 is disclosed in Genbank under access number Gene ID: 5663 and code for the following protein sequence (SEQ ID NO:4):

```
MTELPAPLSYFQNAQMSEDNHLSNTVRSQNDNRERQEHNDRRSLGHPEPL

SNGRPQGNSRQVVEQDEEEDEELTLKYGAKHVIMLFVPVTLCMVVVVATI

KSVSFYTRKDGQLIYTPFTEDTETVGQRALHSILNAAIMISVIVVLTILL

VVLYKYRCYKVIHAWLIISSLLLLFFFSFIYLGEVFKTYNVAVDYITVAL

LIWNFGVVGMISIHWKGPLRLQQAYLIMISALMALVFIKYLPEWTAWLIL

AVISVYDLVAVLCPKGPLRMLVETAQERNETLFPALIYSSTMVWLVNMAE

GDPEAQRRVSKNSKYNAESTERESQDTVAENDDGGFSEEWEAQRDSHLGP

HRSTPESRAAVQELSSSILAGEDPEERGVKLGLGDFIFYSVLVGKASATA

SGDWNTTIACFVAILIGLCLTLLLLAIFKKALPALPISITFGLVFYFATD

YLVQPFMDQLAFHQFYI.
```

In one embodiment, the PS1 protein used according to the invention may be modified (PS1 M146L) and may have the protein sequence sequence (SEQ ID NO: 5) as described below:

```
MTELPAPLSYFQNAQMSEDNHLSNTVRSQNDNRERQEHNDRRSLGHPEPL

SNGRPQGNSRQVVEQDEEEDEELTLKYGAKHVIMLFVPVTLCMVVVVATI

KSVSFYTRKDGQLIYTPFTEDTETVGQRALHSILNAAIMISVIVVMTILL

VVLYKYRCYKVIHAWLIISSLLLLFFFSFIYLGEVFKTYNVAVDYITVAL

LIWNFGVVGMISIHWKGPLRLQQAYLIMISALMALVFIKYLPEWTAWLIL

AVISVYDLVAVLCPKGPLRMLVETAQERNETLFPALIYSSTMVWLVNMAE

GDPEAQRRVSKNSKYNAESTERESQDTVAENDDGGFSEEWEAQRDSHLGP

HRSTPESRAAVQELSSSILAGEDPEERGVKLGLGDFIFYSVLVGKASATA

SGDWNTTIACFVAILIGLCLTLLLLAIFKKALPALPISITFGLVFYFATD

YLVQPFMDQLAFHQFYI.
```

In another embodiment, the vector of the invention comprising a nucleic acid sequence that encodes the APP protein and/or the PS1 or PS2 proteins or variants thereof.

As used herein, the term "PS2" or "Presenilin 2" denotes a protein encoded by the PSEN2 gene. Presenilin 2 is one of the four core proteins in presenilin complex, which mediate the regulated proteolytic events of several proteins in the cell, including gamma secretase. Gamma-secretase is considered to play a strong role in generation of beta amyloid, accumulation of which is related to the onset of Alzheimer's Disease, from the beta-amyloid precursor protein. The cDNA sequence for PS2 is disclosed in Genbank under access number Gene ID: 5664 and code for the following protein (SEQ ID NO:6):

```
MLTFMASDSEEEVCDERTSLMSAESPTPRSCQEGRQGPEDGENTAQWRSQ

ENEEDGEEDPDRYVCSGVPGRPPGLEEELTLKYGAKHVIMLFVPVTLCMI

VVVATIKSVRFYTEKNGQLIYTPFTEDTPSVGQRLLNSVLNTLIMISVIV

VMTIFLVVLYKYRCYKFIHGWLIMSSLMLLFLFTYIYLGEVLKTYNVAMD

YPTLLLTVWNFGAVGMVCIHWKGPLVLQQAYLIMISALMALVFIKYLPEW

SAWVILGAISVYDLVAVLCPKGPLRMLVETAQERNEPFPALIYSSAMVWT

VGMAKLDPSSQGALQLPYDPEMEEDSYDSFGEPSYPEVFEPPLTGYPGEE

LEEEEERGVKLGLGDFIFYSVLVGKAAATGSGDWNTTLACFVAILIGLCL

TLLLLAVFKKALPALPISITFGLIFYFSTDNLVRPFMDTLASHQLYI.
```

In one embodiment, the vector of the invention comprises a nucleic acid sequence that encodes the APP protein and a nucleic acid sequence that encodes the PS2 protein.

In one embodiment, the vector of the invention comprises a nucleic acid sequence that encodes the APP protein, a nucleic acid sequence that encodes the PS1 protein and a nucleic acid sequence that encodes the PS2 protein.

In another embodiment, the vector of the invention may comprises any variant of the nucleic acid sequence which encodes for the APP protein and/or any variant of the nucleic acid sequence which encodes for the PS1 protein and/or variant of the nucleic acid sequence which encodes for the PS2 protein.

In another embodiment, the vector of the invention may comprises any variant of the nucleic acid sequence which encodes for any variant of the APP protein and/or any variant of the nucleic acid sequence which encodes for any variant of the PS1 protein and/or any variant of the nucleic acid sequence which encodes for any variant of the PS2 protein.

The variants include, for instance, naturally-occurring variants due to allelic variations between individuals (e.g., polymorphisms), alternative splicing forms, etc. The term variant also includes genes sequences of the invention from other sources or organisms. Variants are preferably substantially homologous to sequences according to the invention, i.e., exhibit a nucleotide sequence identity of typically at least about 75%, preferably at least about 85%, more preferably at least about 90%, more preferably at least about 95% with sequences of the invention. Variants of the genes of the invention also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

In one embodiment, the vector use according to the invention is a non viral vector or a viral vector.

In a particular embodiment, the non viral vector may be a plasmid comprising a nucleic acid sequence that encodes the APP protein and/or the PS1 protein.

In another particular embodiment, the vector may a viral vector.

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. No. 5,882,877, U.S. Pat. No. 6,013,516, U.S. Pat. No. 4,861,719, U.S. Pat. No. 5,278,056 and WO94/19478.

In a particular embodiment, the viral vector may be an adenoviral, a retroviral, a lentiviral, an herpesvirus or an adeno-associated virus (AAV) vectors.

In a preferred embodiment, adeno-associated viral (AAV) vectors are employed.

In another preferred embodiment, the AAV vector is AAV1, AAV2, AAV3, AAV4, AA5, AAV6, AAV7, AAV8, AAV9, AAV10 or any other serotypes of AAV that can infect human, rodents, monkeys or other species.

In a more preferred embodiment, the AAV vector is an AAV10 or AAV9.

By an "AAV vector" is meant a vector derived from an adeno-associated virus serotype, including without limitation, AAV-1, AAV-2, AAV-3, AAV-4, AAV-5, AAV6, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. ITRs don't need to be the wild-type nucleotide sequences, and may be altered, e.g, by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e. the nucleic acid sequences of the invention) and a transcriptional termination region.

The control elements are selected to be functional in a mammalian cell. The resulting construct which contains the operatively linked components is bounded (5' and 3') with functional AAV ITR sequences. By "adeno-associated virus inverted terminal repeats" or "AAVITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV6, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Particularly preferred are vectors derived from AAV serotypes having tropism for and high transduction efficiencies in cells of the mammalian CNS, particularly neurons. A review and comparison of transduction efficiencies of different serotypes is provided in this patent application. In one preferred example, AAV2 based vectors have been shown to direct long-term expression of transgenes in CNS, preferably transducing neurons. In other non limiting examples, preferred vectors include vectors derived from AAV10 and AAV11 serotypes, which have also been shown to transduce cells of the CNS.

The selected nucleotide sequence is operably linked to control elements that direct the transcription or expression thereof in the subject in vivo. Such control elements can comprise control sequences normally associated with the selected gene.

Alternatively, heterologous control sequences can be employed. Useful heterologous control sequences generally include those derived from sequences encoding mammalian or viral genes. Examples include, but are not limited to, the phophoglycerate kinase (PKG) promoter, CAG, neuronal promoters, promoter of Dopamine-1 receptor and Dopamine-2 receptor, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.). For purposes of the present invention, both heterologous promoters and other control elements, such as CNS-specific and inducible promoters, enhancers and the like, will be of particular use.

Examples of heterologous promoters include the CMV promoter. Examples of CNS specific promoters include those isolated from the genes of myelin basic protein (MBP), glial fibrillary acid protein (GFAP), and neuron specific enolase (NSE).

The AAV expression vector which harbors the DNA molecule of interest bounded by AAV ITRs, can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publications Nos. WO 92/01070 (published 23 Jan. 1992) and WO 93/03769 (published 4 Mar. 1993). Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. In order to produce AAV virions, an AAV expression vector is introduced into a suitable host cell using known techniques, such as by transfection. A number of transfection techniques are generally known in the art. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

For instance, a particular viral vector, such as the AAV10 or AAV9, comprises, in addition to a nucleic acid sequences of the invention, the backbone of AAV vector with ITR derived from AAV-2, the promoter, such as the mouse PGK (phosphoglycerate kinase) gene or the cytomegalovirus/β-actin hybrid promoter (CAG) consisting of the enhancer from the cytomegalovirus immediate gene, the promoter, splice donor and intron from the chicken β-actin gene, the splice acceptor from rabbit β-globin, or any neuronal promoter such as the promoter of Dopamine-1 receptor or Dopamine-2 receptor, or the synapsin promoter, with or without the wild-type or mutant form of woodchuck hepatitis virus post-transcriptional regulatory element (WPRE). The viral vector may comprise in addition, a nucleic acid sequence encoding an antibiotic resistance gene such as the genes of resistance ampicilline (AmpR), kanamycine, hygromycine B, geneticine, blasticidine S or puromycine.

In a particular embodiment, the vector of the invention contains a nucleic acid sequence that encodes the APP protein or APP mutated familiar forms (for example Tottori, Flemish, Arctic, Dutch, Iowa, Iranian, Austrian, German, French, Florida, Indiana or Australian mutations) and in particular APPs1 (Swedish and London mutations).

In another particular embodiment, the vector of the invention contains a nucleic acid sequence that encodes the PS1 protein, PS1 M146L, or PS2.

In another particular embodiment, the vector of the invention contains a nucleic acid sequence that encodes the APPs1 protein and a nucleic acid sequence that encodes the PS1 protein.

In another particular embodiment, the vector of the invention contains a nucleic acid sequence that encodes the APPs1 protein and a nucleic acid sequence that encodes the PS1 protein or a nucleic sequence that encodes the PS2 protein.

In another particular embodiment, the vector of the invention contains a nucleic acid sequence that encodes the APPs1 protein, a nucleic acid sequence that encodes the PS1 protein and a nucleic sequence that encodes the PS2 protein.

In a particular embodiment of the invention, the vector of the invention is a viral vector, for example the AAV10 or AAV9 vectors which contains a nucleic acid sequence that encodes the APPs1 protein and a nucleic acid sequence that encodes the PS1 protein M146L and/or a nucleic sequence that encodes the PS2 protein, the gene AmpR, sequences ITR and the promoter CAG.

In a particular embodiment, the vector of the invention is a viral vector, for example the AAV10 or AAV9 vectors which contains a nucleic acid sequence that encodes the APP protein and a nucleic acid sequence that encodes the PS1 protein spaced by a nucleic acid sequence that encodes a self-cleaving peptide (especially T2A peptide) and the promoter CAG.

Methods of the Invention

A second object of the invention relates to a method for inducing the Alzheimer's disease in an animal, said method comprising the administration of at least one vector containing a nucleic acid sequence that encodes the APP protein and/or the PS1 protein or a variant thereof.

In one embodiment, the vector used for inducing the Alzheimer's disease comprises the nucleic acid sequence that encodes the APP protein and the nucleic acid sequence that encodes the PS1 protein.

In another embodiment, the method for inducing the Alzheimer's disease in an animal comprises the administration of a vector containing a nucleic acid sequence that encodes the APP protein or a variant thereof and a vector containing a nucleic acid sequence that encodes the PS1 protein or a variant thereof.

In another embodiment, the method for inducing the Alzheimer's disease in an animal comprises the administration of a vector containing a nucleic acid sequence that encodes the APP protein and a vector containing a nucleic acid sequence that encodes the PS1 protein.

In another embodiment, the method for inducing the Alzheimer's disease in an animal comprises the administration of a vector containing a nucleic acid sequence that encodes the APPs1 protein and a vector containing a nucleic acid sequence that encodes the PS1 protein M146L.

In a particular embodiment, the method for inducing the Alzheimer's disease in an animal comprises the administration of a vector containing a nucleic acid sequence that encodes the APP protein and/or a vector containing a nucleic acid sequence that encodes the PS1 protein and/or a vector containing a nucleic acid sequence that encodes the PS2 protein.

In another particular embodiment, the method for inducing the Alzheimer's disease in an animal comprises the administration of a vector containing a nucleic acid sequence that encodes the APP protein and a vector containing a nucleic acid sequence that encodes the PS2 protein.

In another particular embodiment, the method for inducing the Alzheimer's disease in an animal comprises the administration of a vector containing a nucleic acid sequence that encodes the APP protein and a vector containing a nucleic acid sequence that encodes the PS1 protein and a vector containing a nucleic acid sequence that encodes the PS2 protein.

Particularly, the method according to the invention is not a method of treatment, in particular a method of treatment of the human or animal body by surgery or therapy.

Methods of delivery of vectors to neurons and/or astrocytes of the animal model includes generally any method suitable for delivery vectors to the neurons and/or astrocytes such that at least a portion of cells of a selected synaptically connected cell population is transduced. Vectors may be delivered to any cells of the central nervous system, or both. Generally, the vector is delivered to the cells of the central nervous system, including for example cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof, or preferably any suitable subpopulation thereof. Further preferred sites for delivery include the ruber nucleus, corpus amygdaloideum, entorhinal cortex and neurons in ventralis lateralis, or to the anterior nuclei of the thalamus.

In a particular embodiment, vectors of the invention are delivered by stereotactic injections or microinjections directly in the brain and more precisely in the hippocampus.

To deliver vectors of the invention specifically to a particular region and to a particular population of cells of the CNS, vectors may be administered by stereotaxic microinjection. For example, animals have the stereotactic frame base fixed in place (screwed into the skull). The brain with stereotactic frame base (MRIcompatible with fiducial markings) is imaged using high resolution MRI. The MRI images are then transferred to a computer which runs stereotactic software. A series of coronal, sagittal and axial images are used to determine the target (site of AAV vector injection) and trajectory. The software directly translates the trajectory into 3 dimensional coordinates appropriate for the stereotactic frame. Holes are drilled above the entry site and the stereotactic apparatus positioned with the needle implanted at the given depth. The AAV vector is then injected at the target sites. Since the AAV vector integrates into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

Additional routes of administration may also comprise local application of the vector under direct visualization, e.g., superficial cortical application, or other nonstereotactic application. The vector may be delivered intrathecally, in the ventricules or by intravenous injection.

Preferably, the method of the invention comprises intracerebral administration through stereotaxic injections. However, other known delivery methods may also be adapted in accordance with the invention. For example, for a more widespread distribution of the vector across the CNS, it may be injected into the cerebrospinal fluid, e.g., by lumbar puncture. To direct the vector to the peripheral nervous system, it may be injected into the spinal cord or into the peripheral ganglia, or the flesh (subcutaneously or intramuscularly) of the body part of interest. In certain situations the vector can be administered via an intravascular approach. For example, the vector can be administered intra-arterially (carotid) in situations where the blood-brain barrier is disturbed or not disturbed. Moreover, for more global delivery, the vector can be administered during the "opening" of the blood-brain barrier achieved by infusion of hypertonic solutions including mannitol.

Vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

In another embodiment, the method according to the invention may further comprise injections of molecules that can help to establish the Alzheimer's disease in animals. For example, the protein ApoE can be injected or overexpressed to the animal to promote the process of establishing the disease.

Thus, the invention may relates to a method for inducing the Alzheimer's disease in an animal, said method comprising the administration of at least one vector containing a nucleic acid sequence that encodes the APP protein and/or the PS1 protein or a variant thereof and the protein ApoE.

In another embodiment, the method for inducing the Alzheimer's disease in an animal comprises the administration of a vector comprising the nucleic acid sequence that encodes the APPs1 protein and the nucleic acid sequence that encodes the PS1 protein and the protein ApoE.

In another embodiment, the method for inducing the Alzheimer's disease in an animal comprises the administration of a vector containing a nucleic acid sequence that encodes the APP protein and a vector containing a nucleic acid sequence that encodes the PS1 protein and the protein ApoE.

Particularly, a vector containing a nucleic acid sequence that encodes the protein ApoE may be use in the method according to the invention.

Particularly, a vector containing a nucleic acid sequence that encodes the protein ApoE2 or ApoE3 or ApoE4 may be use in the method according to the invention As used herein, the term "protein ApoE" denotes a protein which confers a risk for Alzheimer and cardiovascular disease. The ApoE gene codes for a protein which is implicated in the cholesterol regulation. There are three relatively common allelic variants of ApoE (accession number: NP_000032.1) known as ApoE2, ApoE3, and ApoE4. The most common variant overall is ApoE3 which is neutral. ApoE2 protect while ApoE4 confers a higher risk for Alzheimer and cardiovascular disease.

In another aspect, the invention relates to a vector containing a nucleic acid sequence that encodes the APP mutated familiar forms (for example Tottori, Flemish, Arctic, Dutch, Iowa, Iranian, Austrian, German, French, Florida, Indiana or Australian mutations) and in particular APPs1 and/or the PS1 protein for use in a method for inducing the Alzheimer's disease in an animal.

Animals of the Invention

A third object of the invention relates to an animal having the Alzheimer's disease, said animal being obtained by the method according to the invention.

An animal obtained by the method of the invention will preferably display increased production of amyloid peptides, hyperphosphorylation of endogenous Tau protein and cognitive deficits, parameters which are characteristics of Alzheimer's disease.

Thus, in a specific embodiment, said animal is for use as a model of Alzheimer's disease. The invention further relates to the use of an animal having increased production of amyloid peptides, hyperphosphorylation of endogenous Tau protein and cognitive deficits as a model of Alzheimer's disease, said animal being obtained by the method of the invention.

The animal obtained by the method of the invention may be of any species. It may for instance be a rodent or a non-human primate. Particularly, the animal obtained by the method of the invention is not a human. Typically, the animal obtained by the method of the invention may be a rat, a mouse or a macacus microceb. The animal may be a genetically modified animal, such as a 'knockout' animal in which the function or expression of a gene has been reduced or eliminated.

Animals obtained by the method of the invention can be easily distinguished from prior art Alzheimer models and offer many advantages (see examples).

Indeed, contrary to prior art transgenic animals, animals obtained by the method of the invention can be obtained rapidly e.g. in one month and can be obtained in several animal lines for example in most of the mouse lines. Moreover, the animal obtained by the method of the invention overcomes two major drawbacks of transgenic models: 1) continuous transgenes expression from in utero, 2) limitation of the transgenesis to mice.

Furthermore, contrary to animal obtained by injection, animals obtained by the method product all neurotoxic metabolites derived from APP (Aβ42 and βCTF), in a continuous manner and in a pathophysiologic level.

Methods of Screening of the Invention

Such animal model may for instance be of major interest for industrial validation of current and future treatments against this disease.

Therefore, in a fourth object, the invention relates to a method of screening a compound for therapeutic use in the treatment of Alzheimer's disease, using the animal of the invention.

The invention also concerns the use of said animal for assessing potential side-effects of treatment of Alzheimer's disease. Said treatment may include, for example, administration of therapeutic compounds that act on APP accumulation, as described below.

The compound to be screened for therapeutic use against Alzheimer's disease may be used for preventing or treating Alzheimer's disease. Such compound may be any kind of compound that may act Alzheimer's disease. It may for instance decrease accumulation of APP and/or decrease accumulation of neurotoxic metabolites derived from APP (Aβ42 and βCTF) for example. The compound to be screened for therapeutic use against Alzheimer's disease should preferably display a low toxicity.

The screening may for instance include the steps of administering a compound to be screened to the animal of the invention, waiting for a certain period of time, optionally repeating the administration, measuring the accumulation of APP and/or neurotoxic metabolites, and selecting the compound according to its effect on the accumulation of APP and/or neurotoxic metabolites. For example, if the compound tested allows a decrease of the accumulation of APP and/or neurotoxic metabolites, it could be select as potential therapeutic drug against Alzheimer's disease.

Alternatively, the animal of the invention may also be for use for studying the mechanism of Alzheimer's disease. Another embodiment concerns the use of an animal having Alzheimer's disease for studying the mechanism of the disease, said animal being obtained by the method of the invention. For instance, such an animal can be useful for understanding the physio-pathology or the molecular mechanism involved in Alzheimer's disease.

The invention will be further illustrated by the following figures and examples. However, these examples and figures should not be interpreted in any way as limiting the scope of the present invention.

FIGURES

Figure 1:
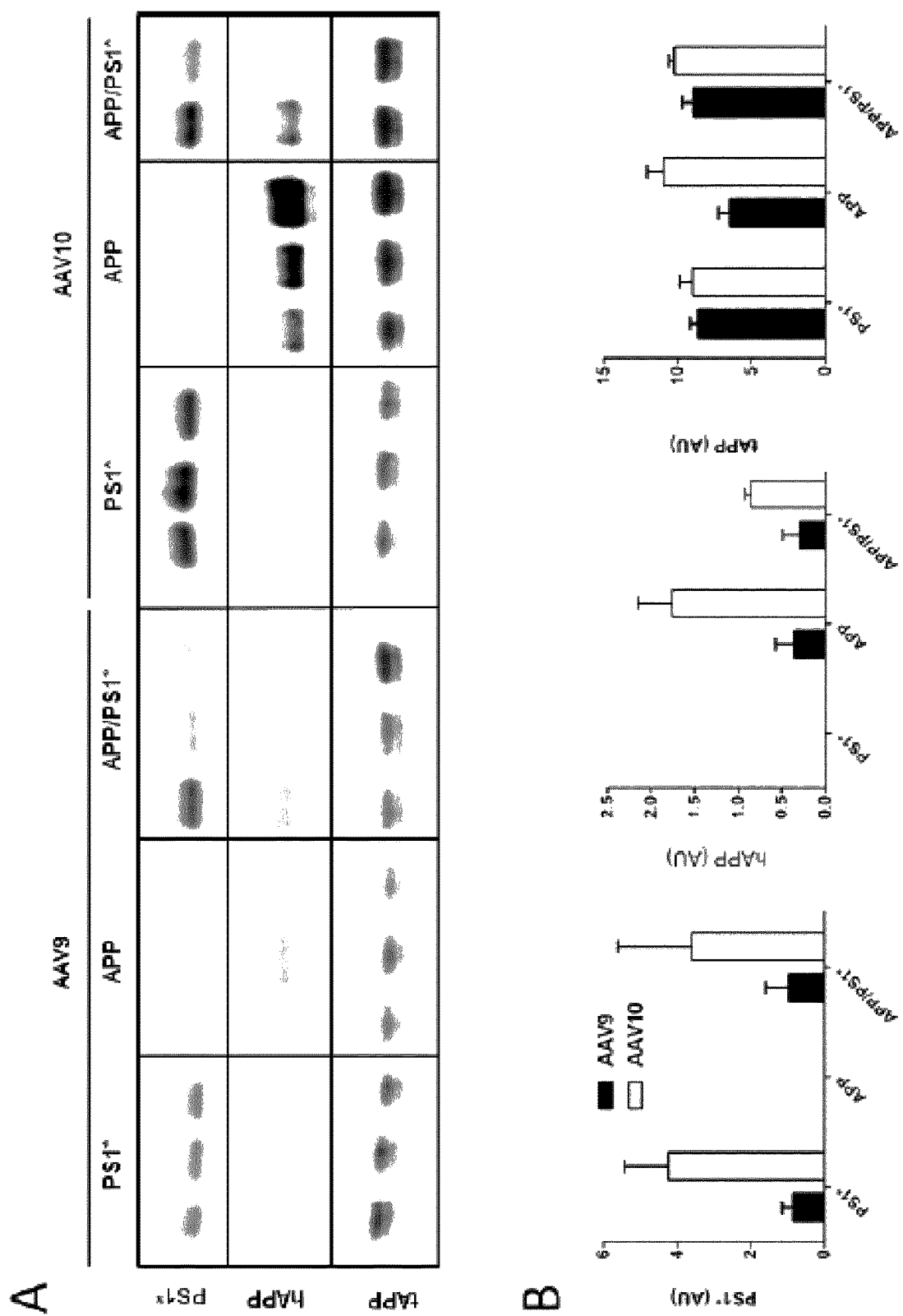

FIG. 1. Western blot analysis of transgene expression. (A) Representative Western blots of PS1 M146L, human APP (hAPP) and human+murine APP (total APP: tAPP) in hippocampus homogenates transduced by AAV9 or AAV10 vectors carrying the PS1 M146L (PS1*), APPs1 (APP) and/or APPs1+PS1 M146L (APP/PS1*) transgenes. (B) A densitometric analysis of the immunoreactivities to the antibodies shown in panel A confirms effective expression of our transgenes.

Figure 2:
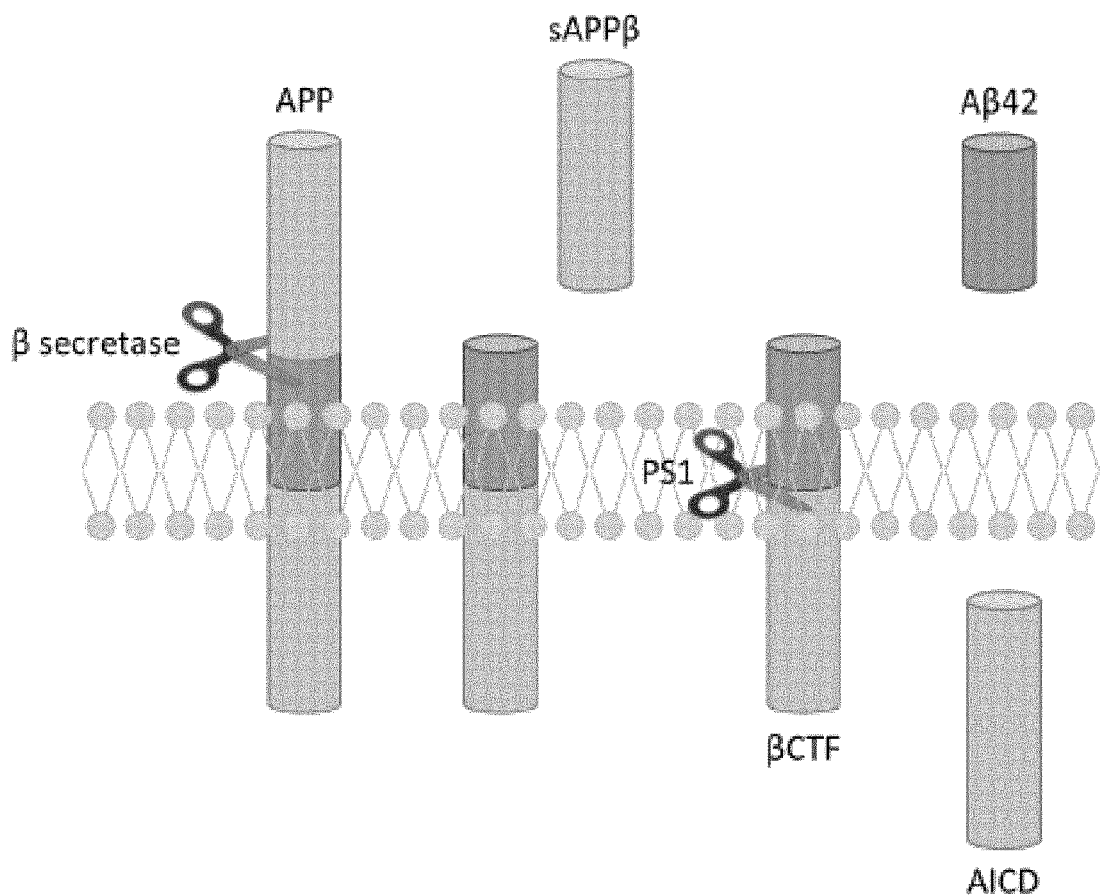

FIG. 2. Amyloidogenic processing of APP. APP protein is cleaved by the β secretase which leads to the production of soluble fragment sAPPβ and βCTF fragment that remains anchored in the membrane. The βCTF is then cleaved by the PS1 (belonging to the γ secretase complex) allowing production of Aβ42 and Aβ40 peptides.

Figure 3:
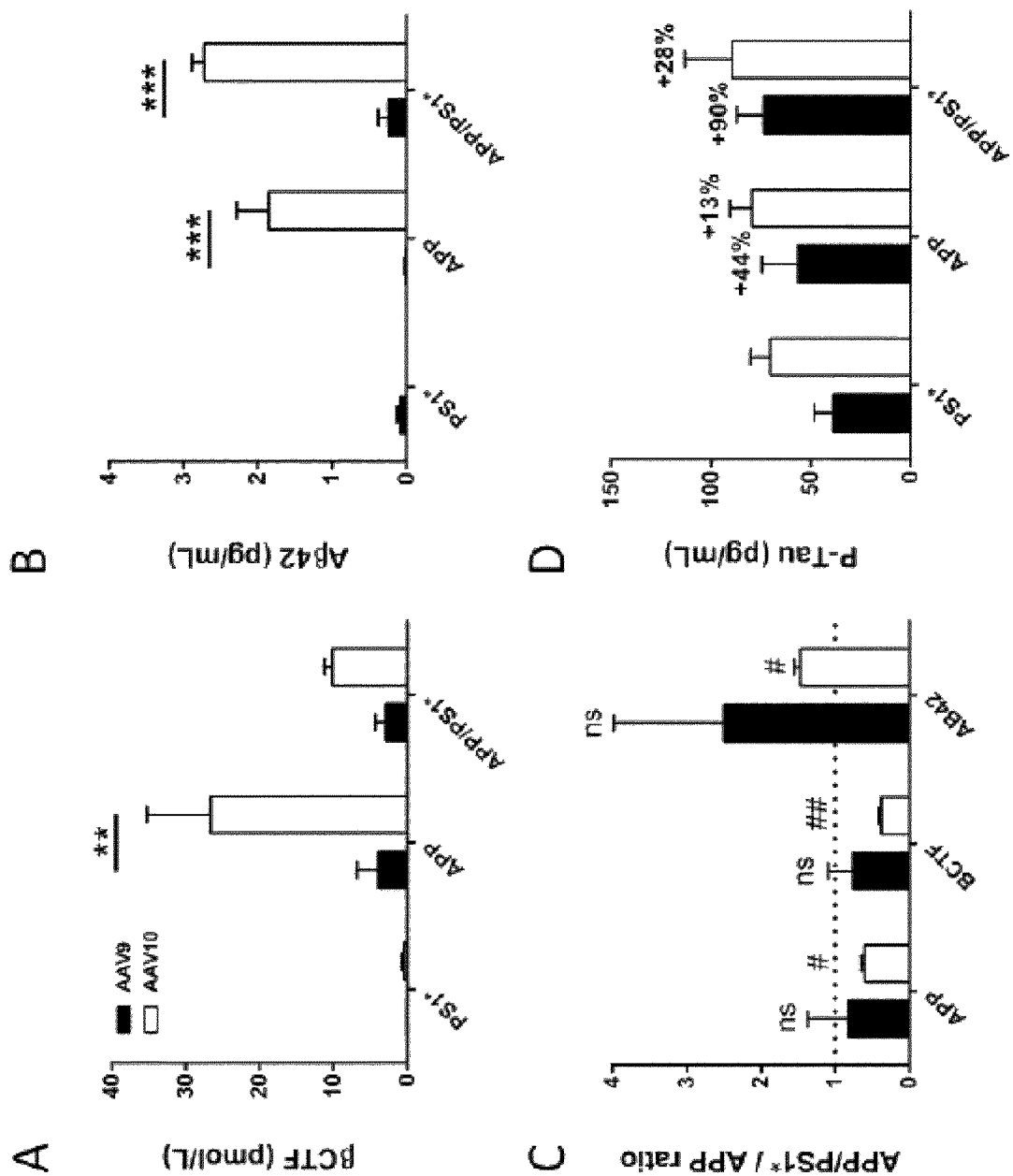

FIG. 3. Simultaneous intracerebral injection of AAV10-APPs1 and AAV10-PS1 M146L in 8 weeks old C57BL/6J mice induce amyloid cascade one month after injection. APP is metabolized to (A) βCTF and then (B) Aβ42 peptide. (C) In contrast to APP and βCTF that decreased with PS1 M146L overexpression, Aβ42 production is increased confirming the interest of the simultaneous intracerebral injection of both vectors. (D) In accordance, abnormal phosphorylation on Threonine residue 181 of murine Tau was stimulated by the double injection of AAV coding for APP and PS1 M146L genes. In all cases, AAV10 induced greater production of neurotoxic metabolites.

Figure 4:
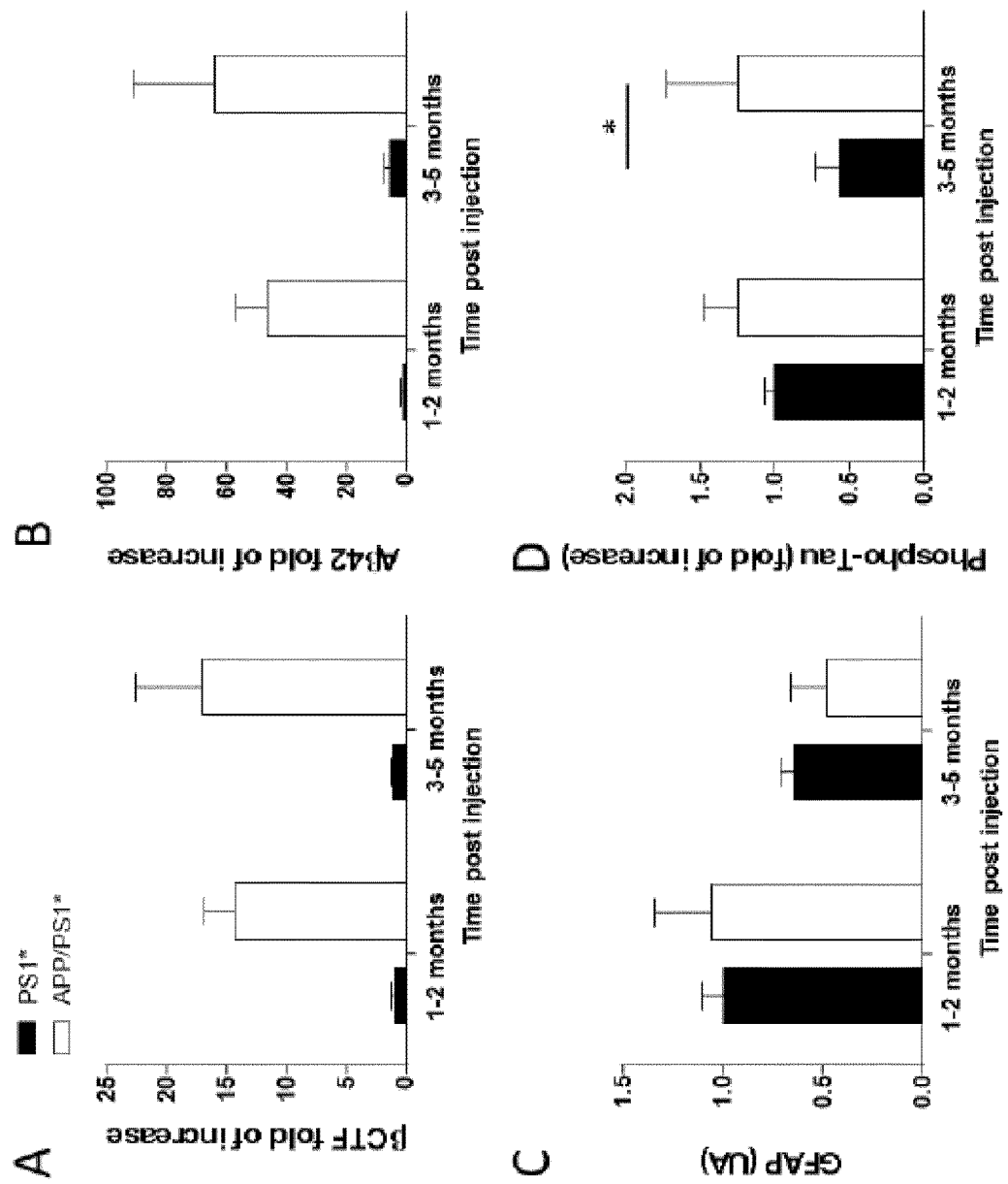

FIG. 4: Simultaneous intracerebral injection of AAV10-APPs1 and AAV10-PS1 M146L in 8 weeks old C57BL/6J mice induce amyloid cascade at least up to five months. (A) The amyloidogenic pathway of APP involved in AD leads to the production of two metabolites of the neurotoxic APP peptides, Aβ42 and βCTF into hippocampus. (B) Hippocampal injection of AAV10 vectors encoding the APPs1 and PS1 M146L proteins allowed, within the first month, the induction of a significant production of Aβ42 as well as βCTF.

This production was stable with time (analyzed up to 5 months). (C-D) The presence of neurotoxic metabolites of APP did not induce astrocytosis as determined by a stable expression of the Glial acidic fibrillatory protein (GFAP) (C) but led to increased levels of phosphorylated endogenous Tau (D) in mice hippocampus between 3 and 5 post-injection.

Figure 5:
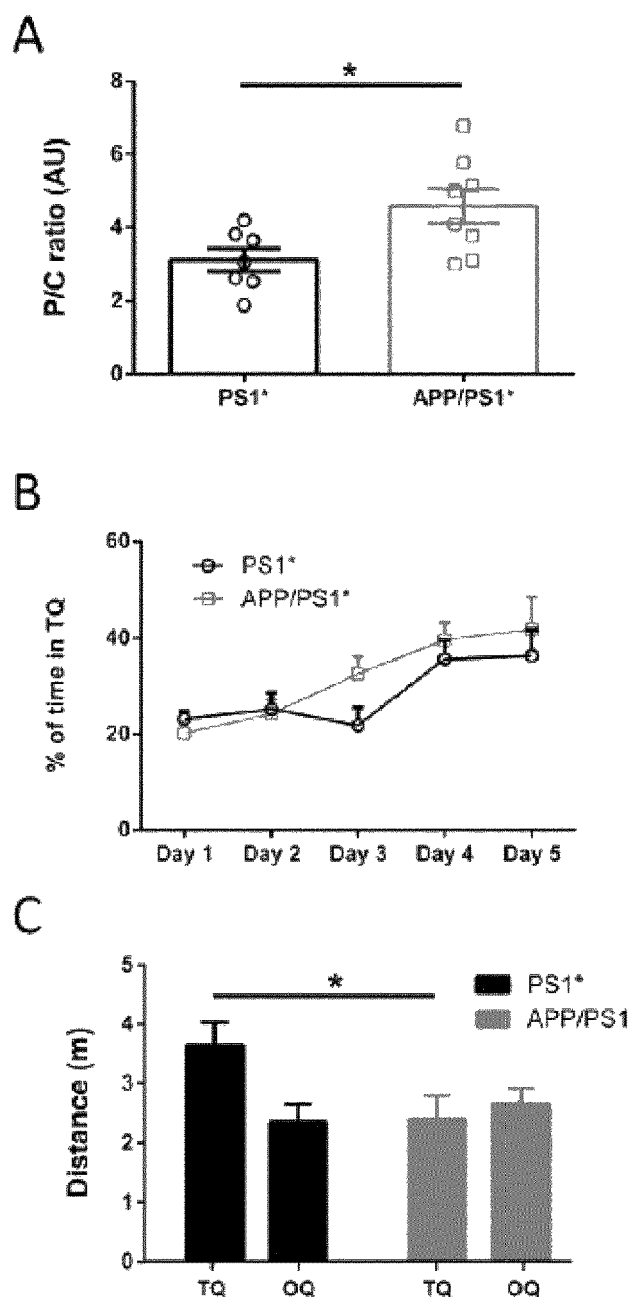

FIG. 5: Cognitive deficits following simultaneous intracerebral injection of AAV-APPs1 and AAV-PS1 M146L. Openfield: (A) Measurement of anxiety levels by analysis of time spent in the periphery relative to the time spent in the center of the apparatus (P/C ratio). The ratio rises when the anxiety of mice rises too. APPs1/PS1 M146L mice thus appeared hyper-anxious compared to PS1 M146L mice (=0.05). Morris water maze: (B) Both groups, APPs1/PS1 M146L and PS1 M146L mice, had an equivalent learning abilities. This learning was confirmed by the appearance of a spatial bias between learning days 1 and 5. (C) Unlike APPs1/PS1 M146L mice, PS1 M146L mice showed a significant preference for the target quadrant suggesting a long term memory impairment of APPs1/PS1 M146L mice 72 hours after learning session (n=8 mice per group).

FIG. 6: AAV-APP and AAV-PS1 co-injection leads to AD-like production levels of amyloid derivatives. (A) Human APP quantification (6e10 antibody) of hippocampus samples showing a comparison between AAVs injected animals (5 months old, 3 months post-injection, n=3 per group), human controls and AD cases (n=5 per group) and APP/PS1ΔE9 mice (5 months old, n=3). APP levels were normalized to GAPDH. Data are means±s.e.m. One Way Anova: *p<0.0001. (B) βCTF comparative analysis by ELISA between human controls and AD cases, AAV co-injected animals and APP/PS1ΔE9 mice at 5, 14 and 16 months old (n=5, 5, 4, 4, 3, 8, 8 per group respectively). Data are means±s.e.m. One Way Anova: *p<0.001. (C) Representation of Aβ40/Aβ42 ratio for the same groups described in panel (B). Data are means±s.e.m. One Way Anova: p<0.01; *p<0.001.

FIG. 7: AAV-APP and AAV-PS1 co-injection allows a hyperphosphorylation of the murine Tau protein from 1 month post-injection. (A) P-Tau (AT270, Thr181) comparative analysis by ELISA between AAV10 injected animals (1 month post-injection, n=3-5 mice per group). (B) GSK-3β comparative analysis by ELISA between AAV10 injected animals (n=3-5 mice per group). One Way Anova: *p<0.05. (C) P-Tau (AT270, Thr181) comparative analysis by ELISA showing significant higher levels in the APP/PS1 group at 3 months post-injection (n=3-5 mice per group). One Way Anova: *p<0.05. (D) Evolution of endogenous Tau hyperphosphorylation over time using four independent experiments with 1 or 3 months old mice (n=17-24 mice per group). Two Way Anova: *p<0.05 (Time effect); **p<0.005 (Group effect).

FIG. 8: AAV-APP and AAV-PS1 co-injection causes a neuronal network failure 3 months post-injection. (A) Western-blot analysis of PSD-95 performed from hippocampus samples showing a comparison between PS1 and APP/PS1 mice at 3 months post-injection (n=4 per group). Data are means±s.e.m and were normalized by GAPDH. t-test, p=0.007. (B) Tonic Glutamatergic Current recorded at a holding potential of +40 mV by whole-cell patch-clamp of CA1 pyramidal neurons.

FIG. 9: AAV-APP and AAV-PS1 co-injection leads to a reduction of gabaergic synaptic marker Gad65. (A) Western-blot analysis of Gad65 performed from hippocampus samples showing a comparison between PS1 and APP/PS1 mice at 3 months post-injection (n=4 per group). Data are means±s.e.m and were normalized by GAPDH. t-test. (B) Western-blot analysis of Gad65 performed from hippocampus samples showing a comparison between human controls and AD cases (n=5 per group). Data are means±s.e.m and were normalized by GAPDH. t-test.

TABLE 1

Comparative table of some AAV models of AD.
Comparative view of some AD models induced by AAV injection. This comparative analysis is based on classical specifications in AD like neurotoxic peptides production and behavioral failures.

| "AAV models" | Species | Number of viruses | Overexpressed proteins | Peptides production | | | | Phosphorylated Tau | Memory defects | Behavioral defects |
|---|---|---|---|---|---|---|---|---|---|---|
| | | | | APP | Aβ42 | Aβ40 | β-CTF | | | |
| AAV-APP.SLA (Jaworski et al.) | Mouse | 1 | APPsla | Yes | ND | ND | ND | Yes | ND | Yes |
| AAV-BRI-Aβ42 (Lawlor et al.) | Rat | 1 | Aβ42 | No | Yes | No | No | ND | No | Yes |
| AAV-BRI-Aβ40 (Lawlor et al.) | Rat | 1 | Aβ40 | No | No | Yes | No | ND | No | Yes |
| AAV-BRI-Aβ42/AAV-BRI-Aβ40 (Lawlor et al.) | Rat | 2 | Aβ42 & Aβ40 | No | Yes | Yes | No | ND | No | Yes |
| AAV-APPsw (Lawlor et al.) | Rat | 1 | APPsw | Yes | No | Yes | ND | ND | No | ND |
| AAV-Aβ42 (Drummond et al.) | Mouse | 1 | Aβ42 | No | No | No | No | ND | ND | ND |
| AAV-Aβ40 (Drummond et al.) | Mouse | 1 | Aβ40 | No | No | No | No | ND | ND | ND |
| AAV-C100 (Drummond et al.) | Mouse | 1 | β-CTF | No | No | No | Yes | ND | ND | ND |
| AAV-Tau-P301L (Jaworski et al.) | Mouse | 1 | Tau | No | No | No | No | Yes | ND | ND |
| Model of the invention | Mouse | 2 | APPsl & PS1* | Yes | Yes | No | Yes | Yes | Yes | Yes |

TABLE 2

Comparative table of some transgenic models of AD.
Update of transgenic animal models of AD with a comparison of neurotoxic peptides and cognitive functions onset.

| "Gold standard models" | Overexpressed proteins | Aβ42 (in months) | B-CTF (in months) | Phosphorylated Tau (in months) | Memory defects (in months) | Behavioral defects (in months) |
|---|---|---|---|---|---|---|
| PDAPP (Weiss et al.) | APP | 8 | | | 13 | 3 |
| Tg2576 (Westerman et al.) | APP | 6 | | | 6 | |
| TgAPP23 (Wolf et al.) | APP | 6 | | 12 | 3 | 10 |
| J20 (Palop et al.) | APP | 2 | | | 6 | |
| TgCRND8 (Nalbantoglu et al.) | APP | 6 | | | 3 | |
| TgCTF104 (Nalbantoglu et al.) | β-CTF | No | Yes | | 8 | |
| TgβCTF99/B6 (Lee et al.) | β-CTF | No | 4 | | 7 | 13 |
| BRI-Aβ42A (McGowan et al.) | Aβ42 | 3 | | | | |
| APPswe/PS1dE9 (Kim et al.) | APPsl & PS1 | 7 | Yes | No | 8 | 7 |
| 5x FAD (Devi et al.) | APPsl & PS1 | 1.5 | | | 4 | |
| JNPL3 (Lewis et al. ) | Tau | No | No | 3 | | |
| V337M tg (Tanemura et al.) | Tau | No | No | 11 | | 11 |
| THY-Tau22 (Schindowski et al.) | Tau | No | No | 3 | 6 | 6 |
| 3x Tg (Oddo et al.) | APPsl, PS1 & Tau | 4 | | | 6 | |
| Model of the invention | APPsl & PS1* | 1 | 1 | 3 | 2.5 | 2.5 |

EXAMPLE

Material & Methods

Tissue Collection

Test mice were anesthetized with ketamine/xylazine and perfused transcardially with 20 ml PBS. One hemisphere was post-fixed for 24 h in 4% PFA, cryoprotected in 30% of sucrose in PBS and cut into 40 µm sections using a freezing microtome for immunohistochemical and histological analyses (data not shown). The other half was frozen immediately on dry ice and used for Western blots and ELISAs.

ELISAs and Western Blots

Mice hippocampal tissue was homogenized in a lysis buffer (TBS, NaCl 150 mM, Triton 1%, Phosphatase and Protease inhibitors) and centrifugated 20' at 13000 rpm. Protein levels were normalized by BCA protein assay (Pierce Biotechnology). Extracted Aβ was then measured using the MSD Human Aβ42 Kit. βCTF was measured using the IBL Human βCTF Kit and the P-Tau using the Innogenetics Phospho-Tau 181P Kit. Aliquots of protein were electrophoretically separated using NuPAGE Bis-Tris Gels (Life Technologies). Electrophoresed proteins were then transferred to nitrocellulose membranes using the iBlot 7-Minute Blotting System, blocked in Tris-buffered saline containing 5% non-fat dry milk and subsequently hybridized with various primary antibodies: APP 6E10 (Sigma), APP Cter (Calbiochem) and Presinilin 1 (Millipore). Densitometry quantification of bands was realised with the BioID software.

Behavioral Analysis

Open Field:

Movement in an open field was used to assess whether APP and PS1 injection had an effect on anxiety which may affect memory and learning behaviors. Mice were placed in the center of a square field. The amount of time spent at the periphery along the walls was recorded as measures of anxiety.

Morris Water Maze:

The Morris water maze (MWM) task quantifies mice memory abilities (Morris, 1984). This test was used as a measure of spatial learning, the mouse must learn the location of a hidden platform by referring to visual cues placed around the room. The platform location was kept constant throughout training but the starting point varied between trials. MWM consists of five consecutive learning days (3 trials per day). Seventy-two hours after the last trial of the fifth day a probe trial is realized to quantify long-term memory. In both testing phases, distance traveled in the quadrant containing the platform or target quadrant is quantified. An effective memory storage must therefore be accompanied by the establishment of a spatial bias characterized by a distance traveled in the target quadrant over than 25%.

Results

Example 1: Relevance of the Animal Model

To evaluate the relevance of our model, we have performed a comparative study between AAV9 and AAV10 vectors encoding the codon-optimized human APP (APPsl, Swedish-London mutations, promoting the cleavage by β secretase complex) and/or PS1 M146L (M146L) transgenes in mice (FIG. 1). Stereotactic injections were performed bilaterally in the hippocampus, an early-affected region in AD.

These results show that the expression of human APPsl by gene transfer leads to lowly increase the total quantity of APP. Co-express with the PS1 M146L, human APP and βCTF amount decrease due to APP metabolization by secretase complexes. Moreover, AAV10 virus seems to be better to efficiently produce human APP in mice than AAV9 virus.

AD is characterized by the amyloidogenic pathway of APP metabolism that results from the cleavage of APP by PS1 (FIG. 2). Animals injected with AAV vector encoding human PS1 M146L protein only (control animal) or with AAV vectors encoding the APPsl and PS1 M146L were sacrificed at 1 month post-injection for histopathological (data not shown), and biochemical and molecular studies (FIG. 3).

We confirmed by immunohistochemistry our results showed in FIG. 1: AAV10 seems to be better than AAV9 to express APP, in particular in CA2 and Subiculum regions of the hippocampus (data not shown). Co-expression of APPsl and PS1 M146L leads to decreased concentration of βCTF as revealed by APP C-ter antibody, or 4G8 antibody staining (data not shown). Expression of PS1 M146L leads to increased metabolism of βCT in Aβ42 peptides as explained in FIG. 2.

Example 2: Production of Metabolites in the Animal Model

APP is cleaved into different metabolites like C-terminal fragment of APP (βCTF) and Aβ42 peptide with characterized neurotoxic properties. We showed that expression of PS1 M146L leads to increased metabolism of βCTF in Aβ42 peptides. Indeed decreased concentration of βCTF is observed in the hippocampus of mice co-injected with AAV10-APPs1 and AAV10-PS1 M146L vectors (FIG. 3).

The amount of βCTF showed respectively a 56- and 25-fold increase for APPs1 and APPs1/PS1 M146L mice compared to PS1 M146L control mice one month after injection (FIG. 3A). Overexpression of human APPs1 thus significantly promotes the production of βCTF. βCTF concentration is decreased in APPs1/PS1 M146L mice compared to APPs1 mice, demonstrating increased metabolism of βCTF with overexpression of PS1 M146L. βCTF was also detected in cortical structures in the absence of cortical production sites which argues for diffusion of βCTF produced into the hippocampus towards the cortical structures (data not shown). Aβ42 (the main neurotoxic peptide in AD) production is, on the other side, strongly increased in APPs1/PS1 M146L mice.

A longitudinal study was performed to analyze the kinetics of neurotoxic peptides production in mouse brain (FIG. 4). A statistically significant (43 fold) increase of Aβ42 peptides production was observed in mice injected with both AAV10-APPs1 and AAV10-PS1 M146L vectors in the hippocampus ($p=0.002$). βCTF production also showed a significant 15-fold increase ($p=0.0001$). In addition, evidence of murine Tau hyperphosphorylation (Threonine residue 181) appeared between 3 and 5 months after injection ($p=0.03$).

Example 3: Behavioral Analysis of the Animal Model

At 2.5 months post-injection, a behavioral study was performed in injected animals (FIG. 5) for a period of 2.5-3 months. The Openfield test was used to evaluate spontaneous locomotion of mice and behavior response to a new environment. The ratio between time spent in the periphery (noted P, area less anxiogenic) and in the center (noted C) of the open field was significantly increased in APPs1/PS1 M146L mice compared to PS1 M146L mice ($p<0.05$), suggesting an increased level of anxiety in APPs1/PS1 M146L mice.

During the learning phase of the Morris water maze test, no learning defect was observed in APPs1/PS1 M146L compared to PS1 M146L control mice The two groups had therefore a normal learning profile. During the restitution phase of acquired information (72 hours retention time), a failure to return to platform quadrant previously acquired was observed in APPs1/PS1 M146L mice. The distance traveled by the mouse PS1 M146L in the target quadrant (TQ) was significantly greater than in other quadrants ($p=0.01$) confirming the presence of a spatial bias. The presence of this spatial bias was not observed for APPs1/PS1 M146L mice ($p=ns$). So APPs1/PS1 M146L mice traveled less distance in the quadrant previously containing the platform. These results confirm a lack of long-term memory in these mice compared to control mouse PS1 M146L ($p=0.02$).

In conclusion, AAV-APPs1 and AAV-PS1 M146L injection in wild type mouse leads to rapid (1 month) and stable (evaluated up to 5 months) increased production of amyloid peptides, hyperphosphorylation of endogenous Tau protein and cognitive deficits in mice, parameters which are characteristics of Alzheimer's disease.

Such models could be useful to analyze deleterious mechanisms induced by amyloid pathway, as well as to evaluate biomarkers or screen therapeutic approaches.

Example 4: Advantages of Animal Model of the Invention from Other Models

The generation of AD animal models aims to reproduce symptoms, injuries or causes similar to those observed in the human disease. Many strains of transgenic mice are successful to reproduce these lesions: extracellular deposits of Aβ peptide and intracellular accumulation of Tau protein. However the existing models are imperfect. To identify new therapeutic targets and the effectiveness of treatments in AD, various pharmaceutical companies have developed their own mouse models. Some companies also developed/used different models for provision of services as Contract Research Organizations (CROs).

These models have specific drawbacks:
Transgenic models have an important expression of transgenes from the embryonic stages of development which will ultimately lead to the establishment of adaptive mechanisms. In addition, the cost of production is very high. They often imperfectly reproduce the AD phenotype and are difficult to transpose to larger species. Obtain models of AD in large species (rats and primates in particular) would be crucial to develop biomarkers and validate therapeutic approaches in a context as close as possible to the human pathophysiology.
Models by intracerebral injection of amyloid peptides, truncated or not, are very easy to develop, relatively inexpensive and do not induce adaptive mechanisms. However, they suffer from several drawbacks: in addition to providing a partial model of AD, they do not have all the neurotoxic products generated in AD and in particular βCTF, products described as highly neurotoxic even at low doses. The administered concentrations of Aβ42 or 25-35 are much higher than those observed in human pathological conditions. These models are therefore particularly suitable for measuring the neuroprotective ability of drugs but have a reduced interest to characterize compounds that modulate the pathological APP metabolism or intracellular changes resulting from the production of neurotoxic metabolites derived from APP.

In comparison with current transgenic models, the present AAV-APPs1/AAV-PS1 M146L model offers many advantages (see table 2):
No establishment of breeding colony, but induction of "on-demand model", on standard commercial animals with an expression of toxic metabolites of APP at one month after injection: saving time (at least one year for the establishment of sufficient colony to produce experimental batches) and financial gain (no need to decontaminate strains before implantation nor to keep the breeding continuously).
Ability to induce amyloid pathology in specific transgenic mouse lines. It could be useful to determine the involvement of new therapeutic targets (for example to understand a hypothetic involvement of the kinase DIRK1A in AD we could induce the amyloid pathology by these constructions in a model of mice over-expressing DIRK1A protein).

The use of a model by gene transfer overcomes two major drawbacks of transgenic models: 1) continuous transgenes expression from in utero, 2) limitation of the transgenesis to mice. The transfer of this technology in other species (particularly rats & non-human primates) will allow imaging studies, search for biomarkers in cerebrospinal or blood fluids and more advanced cognitive tests.

As compared to models by injection, our model has many advantages (see table 1):

Production of all neurotoxic metabolites derived from APP (Aβ42 and βCTF)
Continuous production of all neurotoxic APP derivatives
Pathophysiologic production level Thus, a mouse model (and/or rat) of Alzheimer's disease by gene transfer would be a powerful tool that would combine the advantages of transgenic animals (complete and stable modeling of the amyloid cascade) without the inconvenience of adaptive mechanisms, and with reduced production costs. Such model could be a major alternative for companies like CROs.

Example 5: Gene Transfer Leads to APP and Cleavage Products Levels Close to Humans In order to confirm the relevance of this strategy compared to human physiopathology, we performed a comparative study between hippocampus homogenates from 3 months old APP/PS1 mice, human samples (age matched non dementia controls & AD Braak 6/Thal 5 patients; n=5/group) and 5 months old APP/PS1ΔE9 commonly used as gold standard.

An APP decrease was observed in both pathologic groups i.e. AAV-APP/PS1 and AD Braak VI Thal V patients (FIG. 6A) in comparison to their respective controls. In contrast to APP/PS1 mice, a significant higher amount of human APP (n=3-5 samples per group, *p<0.0001) was measured in APP/PS1ΔE9 transgenic mice (FIG. 6A) which furthermore increase with age (data not shown). We further evaluated the total APP amount (murine+human forms). Strikingly, there was no significant overproduction of total APP in contrast to APP/PS1ΔE9 mice (data not shown). No APP accumulation over time was measured during at least 12 months post-injection. We then evaluated catabolites derived from the amyloidogenic pathway in the hippocampus. First of all, βCTF levels were similar between APP/PS1 mice and AD patients. Significant higher levels were measured in APP/PS1ΔE9 mice confirming age-dependent APP and βCTF accumulation in these animals (FIG. 6B; n=3-8 samples per group, *p<0.0001). Thus, ELISA revealed APP/PS1 Aβ42 amounts comprised between controls and AD patients. Higher levels were observed in transgenic mice. In addition, no significant difference appeared between Aβ40 levels between human samples and AAV mice unlike with transgenic samples. We finally calculated the Aβ40/Aβ42 ratio and similar values were obtained between AD patients and APP/PS1 group. Interestingly it appeared that 16 months old is not sufficient to obtain the same ratio in APP/PS1ΔE9 mice (FIG. 6C). Altogether, our data strongly suggest that amyloid processing due to AAV injection is closer humans that transgenic APP/PS1dE9 mice.

Example 6: APP/PS1 Co-Injection Triggers a Hyperphosphorylation of the Endogenous Tau Protein Given the evidence that human APP is processed following the amyloidogenic pathway we examined the potential impact on the hyperphosphorylation of the murine Tau. We detected an increase in the APP/PS1 group (n=4) compared to the APP (n=4) and PS1 (n=4) groups (FIG. 7A). We also measured a higher amount of GSK-3β, key kinase implicated in the Tau phosphorylation (FIG. 7B). ELISA assay realized on 3 months old APP/PS1 mice showed thereby a significant hyperphosphorylation of Tau (FIG. 7C; n=3-4 mice per group, *p<0.05). To ensure that there is indeed a trend concerning the phosphorylation state of Tau, we performed a comparative analysis between the APP and APP/PS1 group normalized on PS1 group (FIG. 7D). Data cumulated from four different experiments with 1 or 3 months old mice were used (n=17-24 mice per group) and showed a significant effect of group (**p<0.005) and time (*p<0.05) suggesting an exacerbation of tau phosphorylation over time.

Example 7: APP/PS1 Mice Present a Failure of the Neuronal Network

It is well known that synaptic dysfunctions appear as an early event in AD (Scheff et al., 2007). Some synaptic markers like PSD-95 have been showed as reduced in AD patients (Proctor et al., 2010). We evaluated PSD-95 levels in the hippocampus of our model at 3 months post-injection. A significant decrease appeared in the APP/PS1 group compared to PS1 group (FIG. 8A; n=4 per group, p=0.007). Whole-cell patch-clamp recording of CA1 pyramidal cells was performed and Tonic Glutamatergic Current was recorded. Significant increase appeared in the APP/PS1 group meaning that Glutamate activate preferentially extra-synaptic NMDARs in this group (FIG. 8B; n=11-19 per group).

Example 8: APP/PS1 Mice Present an Altered GABA Pathway

Increasing evidences appeared these past few years about a decreased GABAergic signaling in AD patients (Gang et al., 2009; Xue et al., 2014; Tiwari et al., 2012). Using a 11.7 Tesla MRI, Magnetic Resonance Spectroscopy analysis was performed on PS1 and APP/PS1 mice at 3 months post-injection (n=6 per group). The region of interest was selected in both hippocampus of each mouse brain (data not shown). Results for the APP/PS1 were normalized to the PS1 values. APP/PS1 mice have significantly lower concentrations of Glutamine (Gln; p=0.017), GABA (p=0.018) and NAA (p=0.04) than PS1 mice indicating a decreased neuronal health and particularly a decreased GABA signaling pathway. No differences were obtained between both groups in the levels of Glu, tNAA, Ins and tChol (data not shown). Glutamine is the precursor of Glutamate which is itself the precursor of the GABA neurotransmitter. To explain why we observed a decrease of Glutamine and GABA but not of Glutamate, we looked for the Gad65 expression. Gad65 is an enzyme which catalyzes the decarboxylation of Glutamate to GABA for neurotransmission. It appeared decreased in the APP/PS1 mice at 3 months after injection compared to PS1 mice (FIG. 9A; n=4 mice per groups, p=0.03). Interestingly, a decrease of Gad65 was also shown in human patients compared to control patients (FIG. 9B; n=5 patients per groups, p=0.1).

Example 9: Injection of the CAG-APP-T2A-PS1 Construct

We generate an AAV vector coding for a fusion protein containing APP and PS1 protein spaced by a self-cleaving peptide (T2A peptide). Mice injected with CAG-APP-T2A-PS1 construction present production of neurotoxic metabolites of APP (βCTF, Aβ38/40/42) close to human amounts. Hyperphosphorylation of murine TAU protein is also observable. These cerebral changes lead to behavioral defects in Morris water maze.

CONCLUSION

The inventors describe here the development of an alternative AAV-based mouse model with two major objectives: create a relevant model closer to human physiopathology and mimic the early stages of AD. This model was obtained by co-injection, in the hippocampus of wild-type mice, of two AAV vectors coding the human Amyloid Protein Precursor (APPs1) and the human Presinilin 1 (PS1M146L). Our strategy allows a stable expression of transgenes without significant APP overexpression. This leads to βAPP production and its neurotoxic catabolites such as sAPPβ, βCTF and Aβ42 as soon as one month post-injection and stable during at least 12 months without classical late symptoms appearance such as senile plaque, inflammation or atrophy. Otherwise, they measured very close amounts of APP, βCTF and Aβ peptides compared to human homogenates and unlike what we can find in APP/PS1ΔE9 mice. Interestingly, only co-injection triggered hyperphosphorylation of the murine Tau protein resulting from an increase of GSK-3β levels. Finally, significant behavior impairments appeared from 3 months post-injection in association with an alteration of synaptic functions especially a decrease of PSD-95 associated with synaptic defects such as extrasynaptic NMDAR activity and an alteration in the GABAergic pathway.

REFERENCES

Throughout this application, various references describe the state of the art to which this invention pertains. The disclosures of these references are hereby incorporated by reference into the present disclosure.

Cartier, N. et al. Hematopoietic stem cell gene therapy with a lentiviral vector in X-linked adrenoleukodystrophy. Science 326, 818-823, doi:10.1126/science.1171242 (2009).

Deglon, N. & Hantraye, P. Viral vectors as tools to model and treat neurodegenerative disorders. The journal of gene medicine 7, 530-539, doi:10.1002/jgm.707 (2005).

Devi, L. & Ohno, M. Phospho-eIF2alpha level is important for determining abilities of BACE1 reduction to rescue cholinergic neurodegeneration and memory defects in 5xFAD mice. PloS one 5, e12974, doi:10.1371/journal.pone.0012974 (2010).

Drummond, E. S. et al. Pathology associated with AAV mediated expression of beta amyloid or C100 in adult mouse hippocampus and cerebellum. PloS one 8, e59166, doi:10.1371/journal.pone.0059166 (2013).

Jaworski, T. et al. AAV-tau mediates pyramidal neurodegeneration by cell-cycle re-entry without neurofibrillary tangle formation in wild-type mice. PloS one 4, e7280, doi:10.1371/journal.pone.0007280 (2009).

Kayed, R. et al. Common structure of soluble amyloid oligomers implies common mechanism of pathogenesis. Science 300, 486-489, doi:10.1126/science.1079469 (2003).

Kim, T. K. et al. Analysis of differential plaque depositions in the brains of Tg2576 and Tg-APPswe/PS1dE9 transgenic mouse models of Alzheimer's disease. Experimental & molecular medicine 44, 492-502, doi:10.3858/emm.2012.44.8.056 (2012).

Kirik, D. et al. Parkinson-like neurodegeneration induced by targeted overexpression of alpha-synuclein in the nigrostriatal system. The Journal of neuroscience: the official journal of the Society for Neuroscience 22, 2780-2791, doi:20026246 (2002).

Lawlor, P. A. et al. Novel rat Alzheimer's disease models based on AAV-mediated gene transfer to selectively increase hippocampal Abeta levels. Molecular neurodegeneration 2, 11, doi:10.1186/1750-1326-2-11 (2007).

Lee, J. E. & Han, P. L. An update of animal models of Alzheimer's disease with a reevaluation of plaque depositions. Experimental neurobiology 22, 84-95, doi: 10.5607/en.2013.22.2.84 (2013).

Lee, K. W. et al. Progressive neuronal loss and behavioral impairments of transgenic C57BL/6 inbred mice expressing the carboxy terminus of amyloid precursor protein. Neurobiology of disease 22, 10-24, doi:10.1016/j.nbd.2005.09.011 (2006).

Lewis, J. et al. Enhanced neurofibrillary degeneration in transgenic mice expressing mutant tau and APP. Science 293, 1487-1491, doi:10.1126/science.1058189 (2001).

Lo Bianco, C., Ridet, J. L., Schneider, B. L., Deglon, N. & Aebischer, P. alpha—Synucleinopathy and selective dopaminergic neuron loss in a rat lentiviral-based model of Parkinson's disease. Proceedings of the National Academy of Sciences of the United States of America 99, 10813-10818, doi:10.1073/pnas.152339799 (2002).

Nalbantoglu, J. et al. Impaired learning and LTP in mice expressing the carboxy terminus of the Alzheimer amyloid precursor protein. Nature 387, 500-505, doi:10.1038/387500a0 (1997).

McGowan, E. et al. Abeta42 is essential for parenchymal and vascular amyloid deposition in mice. Neuron 47, 191-199, doi:10.1016/j.neuron.2005.06.030 (2005).

Oddo, S., Caccamo, A., Kitazawa, M., Tseng, B. P. & LaFerla, F. M. Amyloid deposition precedes tangle formation in a triple transgenic model of Alzheimer's disease. Neurobiology of aging 24, 1063-1070 (2003).

Palop, J. J. et al. Neuronal depletion of calcium-dependent proteins in the dentate gyrus is tightly linked to Alzheimer's disease-related cognitive deficits. Proceedings of the National Academy of Sciences of the United States of America 100, 9572-9577, doi:10.1073/pnas.1133381100 (2003).

Schindowski, K. et al Alzheimer's disease-like tau neuropathology leads to memory deficits and loss of functional synapses in a novel mutated tau transgenic mouse without any motor deficits. The American journal of pathology 169, 599-616, doi:10.2353/ajpath.2006.060002 (2006).

Selkoe, D. J. Presenilin, Notch, and the genesis and treatment of Alzheimer's disease. Proceedings of the National Academy of Sciences of the United States of America 98, 11039-11041, doi:10.1073/pnas.211352598 (2001).

Tanemura, K. et al. Neurodegeneration with tau accumulation in a transgenic mouse expressing V337M human tau. The Journal of neuroscience: the official journal of the Society for Neuroscience 22, 133-141 (2002).

Weiss, C. et al. Impaired eyeblink conditioning and decreased hippocampal volume in PDAPP V717F mice. Neurobiology of disease 11, 425-433 (2002).

Westerman, M. A. et al. The relationship between Abeta and memory in the Tg2576 mouse model of Alzheimer's disease. The Journal of neuroscience: the official journal of the Society for Neuroscience 22, 1858-1867 (2002).

Wolf, S. A. et al. Cognitive and physical activity differently modulate disease progression in the amyloid precursor protein (APP)-23 model of Alzheimer's disease. Biological psychiatry 60, 1314-1323, doi:10.1016/j.biopsych.2006.04.004 (2006).

The invention claimed is:

1. A method for inducing aspects of Alzheimer's disease in a non-human mammal, said method consisting of co-administering, to the brain of the non-human mammal, a gene encoding Amyloid Precursor Protein (APP) protein and a gene encoding Presenilin 1 (PS1) protein,
wherein the gene encoding the APP protein and the gene encoding PS1 protein are present in at least one vector, and wherein only the APP protein and the PS1 protein are co-expressible from any of said at least one vector; and
wherein co-expression of said APP and said PS1 in the brain of the non-human mammal results in the non-human mammal exhibiting behavior suggestive of anxiety and lack of long term memory; and
wherein co-expression of said APP and said PS1 in the brain of the non-human mammal leads to production of βAPP and neurotoxic catabolites of βAPP from one month after administration and up until at least 12 months after administration without the appearance of classical AD late symptoms; and
wherein the at least one vector is not AAV9.

2. The method according to claim 1 wherein the at least one vector is delivered by stereotactic injections or micro-injections directly into the brain.

3. A non-human mammal having symptoms of Alzheimer's disease wherein the symptoms of Alzheimer's disease are induced by a method consisting of
administering to the non-human mammal at least one vector containing a nucleic acid sequence that encodes an APP protein or a variant thereof and a nucleic acid sequence that encodes a PS1 protein or a variant thereof, and wherein only the APP protein and the PS1 protein are co-expressible from any of said at least one vector,
wherein the at least one vector is not an AAV 9 vector;
wherein co-expression of said APP and said PS1 in the brain of the non-human mammal results in the non-human mammal exhibiting behavior suggestive of anxiety and lack of long term memory; and
wherein co-expression of said APP and said PS1 in the brain of the non-human mammal leads to production of βAPP and neurotoxic catabolites of βAPP from one month after administration and up until at least 12 months after administration without the appearance of classical AD late symptoms.

4. The method of claim 1, wherein the non-human mammal is a rodent or a primate.

5. The method of claim 1, wherein the at least one vector is an AAV10 vector.

6. The non-human mammal of claim 3, wherein the at least one vector is an AAV10 vector.

7. The method of claim 1, wherein the classical AD late symptoms include one or more of deposition of senile plaque, inflammation and atrophy.

8. The method of claim 1, wherein the neurotoxic catabolites of βAPP include one or more of sAPPβ, βCTF and Aβ42.

9. The method of claim 3, wherein the classical AD late symptoms include one or more of deposition of senile plaque, inflammation and atrophy.

10. The method of claim 3, wherein the neurotoxic catabolites of βAPP include one or more of sAPPβ, βCTF and Aβ42.

11. The method of claim 1, wherein the gene encoding the APP protein and the gene encoding the PS1 protein are present on a single vector.

12. The non-human mammal of claim 3, wherein the nucleic acid sequence that encodes an APP protein or a variant thereof and the nucleic acid sequence that encodes a PS1 protein or a variant thereof are present on a single vector.

* * * * *

SEQUENCE LISTING

```
<160> NUMBER OF SEQ ID NOS: 6

<210> SEQ ID NO 1
<211> LENGTH: 2256
<212> TYPE: DNA
<213> ORGANISM: Homo sapiens

<400> SEQUENCE: 1
atgctgcccg gactggctct gctgctgctg gccgcttgga ccgccagagc cctggaagtg      60
cccaccgatg gcaatgctgg cctgctggcc gagccccaga tcgccatgtt ctgcggcaga     120
ctgaacatgc acatgaacgt gcagaacggc aagtgggaca gcgaccccag cggcaccaag     180
acctgcatcg acaccaaaga gggcatcctg cagtattgcc aggaagtgta ccccgagctg     240
cagatcacca acgtggtgga agccaaccag cccgtgacca tccagaactg gtgcaagcgg     300
ggcagaaagc agtgcaagac ccacccccac ttcgtgatcc cttaccggtg cctggtcgga     360
gagttcgtgt ccgacgccct gctggtgccc gacaagtgca agttcctgca tcaggaacgg     420
atggacgtct gcgagacaca tctgcactgg cacaccgtgg ccaaagagac atgcagcgag     480
aagtccacca acctgcacga ctacggcatg ctgctgccct gcggcatcga caagttccgg     540
ggcgtggaat tcgtgtgctg cccctggcc gaggaatccg acaacgtgga cagcgccgac     600
gccgaagagg acgacagcga cgtgtggtgg ggcggagccc acaccgatta cgccgacggc     660
agcgaggaca aggtcgtgga agtggctgaa gaggaagagg tggccgaggt cgaagaagag     720
gaagccgacg acgacgagga tgacgaggac ggcgacgaag tggaagaaga agccgaggaa     780
ccctacgagg aagccaccga gcggaccacc tctatcgcca ccaccaccac aaccactacc     840
gagagcgtgg aagaggtggt gcgcgaagtg tgcagcgagc aggccgagac aggccctgc     900 cgggccatga tcagccggtg gtacttcgac gtgaccgagg gcaagtgcgc cccttcttc     960 tatggcggct gcggcggcaa ccggaacaac ttcgacaccg aggaatactg catggccgtg    1020
tgcggcagcg ccatccctac cacagccgcc agcaccccg acgccgtgga caagtacctg    1080
gaaccccctg gcgacgagaa cgagcacgcc cacttccaga aggccaaaga gcggctggaa    1140
gccaagcacc gcgagcggat gagccaggtg atgagagagt gggaagaggc cgagagacag    1200
gccaagaacc tgcccaaggc cgacaagaaa gccgtgatcc agcacttcca ggaaaaggtc    1260
gaaagcctgg aacaggaagc cgccaacgag cggcagcagc tggtggaaac ccacatggcc    1320
agagtggaag ccatgctgaa cgaccggcgg agactggccc tggaaaacta catcaccgcc    1380
ctgcaggccg tgcccccag acccagacac gtgttcaaca tgctgaagaa atacgtgcgg    1440
gccgagcaga aggaccggca gcacaccctg aagcacttcg agcacgtgcg gatggtggac    1500
cccaagaagg ccgcccagat ccgctctcag gtcatgaccc acctgagagt gatctacgag    1560
agaatgaacc agagcctgag cctgctgtac aatgtgcccg ccgtggccga agaaatccag    1620
gacgaggtgc acgagctgct gcagaaagag cagaactaca gcgacgacgt gctggccaac    1680
atgatcagcg agccccggat cagctacggc aacgacgccc tgatgcccag cctgaccgag    1740
```

-continued

```
acaaagacca ccgtggaact gctgcccgtg aacggcgagt tcagcctgga cgacctgcag    1800
ccctggcaca gctttggcgc tgatagcgtg cccgccaaca ccgagaacga ggtggaaccc    1860
gtggacgcca gacctgccgc cgacagaggc ctgaccacaa gacctggcag cggcctgacc    1920
aacatcaaga ccgaagagat cagcgaagtg aacctggacg ccgagttccg gcacgacagc    1980
ggctacgagg tgcaccacca gaaactggtg ttcttcgccg aggacgtggg cagcaacaag    2040
ggcgccatca tcggcctgat ggtcggaggc gtggtgatcg ccaccgtgat catcatcacc    2100
ctggtgatgc tgaaaaagaa gcagtacacc agcatccacc acggcgtggt cgaagtggac    2160
gccgctgtga cccccgagga acggcacctg agcaagatgc agcagaacgg ctacgagaac    2220
cccacctaca agttcttcga gcagatgcag aactga                              2256
```

<210> SEQ ID NO 2
<211> LENGTH: 751
<212> TYPE: PRT
<213> ORGANISM: Homo sapiens

<400> SEQUENCE: 2

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
```

```
            275                 280                 285
Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Asn Arg Asn Asn Phe Asp Thr Glu Glu Tyr
            325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
            355                 360                 365

His Ala His Phe Gln Lys Ala Lys Glu Arg Leu Glu Ala Lys His Arg
            370                 375                 380

Glu Arg Met Ser Gln Val Met Arg Glu Trp Glu Glu Ala Glu Arg Gln
385                 390                 395                 400

Ala Lys Asn Leu Pro Lys Ala Asp Lys Lys Ala Val Ile Gln His Phe
                405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
                485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
            530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
            595                 600                 605

Ser Val Pro Ala Asn Thr Glu Asn Glu Val Glu Pro Val Asp Ala Arg
            610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Asn Leu Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
            675                 680                 685

Gly Gly Val Val Ile Ala Thr Val Ile Ile Ile Thr Leu Val Met Leu
            690                 695                 700
```

```
Lys Lys Lys Gln Tyr Thr Ser Ile His His Gly Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
            740                 745                 750

<210> SEQ ID NO 3
<211> LENGTH: 751
<212> TYPE: PRT
<213> ORGANISM: Homo sapiens

<400> SEQUENCE: 3

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
```

```
                    325                 330                 335
        Cys Met Ala Val Cys Gly Ser Ala Ile Pro Thr Thr Ala Ala Ser Thr
                        340                 345                 350
        Pro Asp Ala Val Asp Lys Tyr Leu Glu Thr Pro Gly Asp Glu Asn Glu
                        355                 360                 365
        His Ala His Phe Gln Lys Ala Lys Glu Arg Leu Glu Ala Lys His Arg
                        370                 375                 380
        Glu Arg Met Ser Gln Val Met Arg Glu Trp Glu Ala Glu Arg Gln
        385                 390                 395                 400
        Ala Lys Asn Leu Pro Lys Ala Asp Lys Lys Ala Val Ile Gln His Phe
                        405                 410                 415
        Gln Glu Lys Val Glu Ser Leu Glu Gln Glu Ala Ala Asn Glu Arg Gln
                        420                 425                 430
        Gln Leu Val Glu Thr His Met Ala Arg Val Glu Ala Met Leu Asn Asp
                        435                 440                 445
        Arg Arg Arg Leu Ala Leu Glu Asn Tyr Ile Thr Ala Leu Gln Ala Val
                        450                 455                 460
        Pro Pro Arg Pro Arg His Val Phe Asn Met Leu Lys Lys Tyr Val Arg
        465                 470                 475                 480
        Ala Glu Gln Lys Asp Arg Gln His Thr Leu Lys His Phe Glu His Val
                        485                 490                 495
        Arg Met Val Asp Pro Lys Lys Ala Ala Gln Ile Arg Ser Gln Val Met
                        500                 505                 510
        Thr His Leu Arg Val Ile Tyr Glu Arg Met Asn Gln Ser Leu Ser Leu
                        515                 520                 525
        Leu Tyr Asn Val Pro Ala Val Ala Glu Glu Ile Gln Asp Glu Val Asp
        530                 535                 540
        Glu Leu Leu Gln Lys Glu Gln Asn Tyr Ser Asp Asp Val Leu Ala Asn
        545                 550                 555                 560
        Met Ile Ser Glu Pro Arg Ile Ser Tyr Gly Asn Asp Ala Leu Met Pro
                        565                 570                 575
        Ser Leu Thr Glu Thr Lys Thr Thr Val Glu Leu Leu Pro Val Asn Gly
                        580                 585                 590
        Glu Phe Ser Leu Asp Asp Leu Gln Pro Trp His Ser Phe Gly Ala Asp
                        595                 600                 605
        Ser Val Pro Ala Asn Thr Glu Asn Glu Val Glu Pro Val Asp Ala Arg
                        610                 615                 620
        Pro Ala Ala Asp Arg Gly Leu Thr Thr Arg Pro Gly Ser Gly Leu Thr
        625                 630                 635                 640
        Asn Ile Lys Thr Glu Glu Ile Ser Glu Val Lys Met Asp Ala Glu Phe
                        645                 650                 655
        Arg His Asp Ser Gly Tyr Glu Val His His Gln Lys Leu Val Phe Phe
                        660                 665                 670
        Ala Glu Asp Val Gly Ser Asn Lys Gly Ala Ile Ile Gly Leu Met Val
                        675                 680                 685
        Gly Gly Val Val Ile Ala Thr Val Ile Val Ile Thr Leu Val Met Leu
                        690                 695                 700
        Lys Lys Lys Gln Tyr Thr Ser Ile His His Gly Val Val Glu Val Asp
        705                 710                 715                 720
        Ala Ala Val Thr Pro Glu Glu Arg His Leu Ser Lys Met Gln Gln Asn
                        725                 730                 735
        Gly Tyr Glu Asn Pro Thr Tyr Lys Phe Phe Glu Gln Met Gln Asn
                        740                 745                 750
```

```
<210> SEQ ID NO 4
<211> LENGTH: 467
<212> TYPE: PRT
<213> ORGANISM: Homo sapiens

<400> SEQUENCE: 4

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Leu Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
```

```
            370                 375                 380
Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                    405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
                435                 440                 445

Thr Asp Tyr Leu Val Gln Pro Phe Met Asp Gln Leu Ala Phe His Gln
                450                 455                 460

Phe Tyr Ile
465

<210> SEQ ID NO 5
<211> LENGTH: 467
<212> TYPE: PRT
<213> ORGANISM: Homo sapiens

<400> SEQUENCE: 5

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
            35                  40                  45

Pro Leu Ser Asn Gly Arg Pro Gln Gly Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270
```

```
Glu Thr Ala Gln Glu Arg Asn Glu Thr Leu Phe Pro Ala Leu Ile Tyr
                275                 280                 285
Ser Ser Thr Met Val Trp Leu Val Asn Met Ala Glu Gly Asp Pro Glu
290                 295                 300
Ala Gln Arg Arg Val Ser Lys Asn Ser Lys Tyr Asn Ala Glu Ser Thr
305                 310                 315                 320
Glu Arg Glu Ser Gln Asp Thr Val Ala Glu Asn Asp Asp Gly Gly Phe
                325                 330                 335
Ser Glu Glu Trp Glu Ala Gln Arg Asp Ser His Leu Gly Pro His Arg
                340                 345                 350
Ser Thr Pro Glu Ser Arg Ala Ala Val Gln Glu Leu Ser Ser Ser Ile
                355                 360                 365
Leu Ala Gly Glu Asp Pro Glu Glu Arg Gly Val Lys Leu Gly Leu Gly
                370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Phe Val Ala Ile Leu Ile
                405                 410                 415
Gly Leu Cys Leu Thr Leu Leu Leu Ala Ile Phe Lys Lys Ala Leu
                420                 425                 430
Pro Ala Leu Pro Ile Ser Ile Thr Phe Gly Leu Val Phe Tyr Phe Ala
                435                 440                 445
Thr Asp Tyr Leu Val Gln Pro Phe Met Asp Gln Leu Ala Phe His Gln
                450                 455                 460
Phe Tyr Ile
465

<210> SEQ ID NO 6
<211> LENGTH: 447
<212> TYPE: PRT
<213> ORGANISM: Homo sapiens

<400> SEQUENCE: 6

Met Leu Thr Phe Met Ala Ser Asp Ser Glu Glu Val Cys Asp Glu
1               5                   10                  15
Arg Thr Ser Leu Met Ser Ala Glu Ser Pro Thr Pro Arg Ser Cys Gln
                20                  25                  30
Glu Gly Arg Gln Gly Pro Glu Asp Gly Glu Asn Thr Ala Gln Trp Arg
                35                  40                  45
Ser Gln Glu Asn Glu Glu Asp Gly Glu Glu Asp Pro Asp Arg Tyr Val
50                  55                  60
Cys Ser Gly Val Pro Gly Arg Pro Gly Leu Glu Glu Leu Thr
65                  70                  75                  80
Leu Lys Tyr Gly Ala Lys His Val Ile Met Leu Phe Val Pro Val Thr
                85                  90                  95
Leu Cys Met Ile Val Val Ala Thr Ile Lys Ser Val Arg Phe Tyr
                100                 105                 110
Thr Glu Lys Asn Gly Gln Leu Ile Tyr Thr Pro Phe Thr Glu Asp Thr
                115                 120                 125
Pro Ser Val Gly Gln Arg Leu Leu Asn Ser Val Leu Asn Thr Leu Ile
                130                 135                 140
Met Ile Ser Val Ile Val Val Met Thr Ile Phe Leu Val Val Leu Tyr
145                 150                 155                 160
Lys Tyr Arg Cys Tyr Lys Phe Ile His Gly Trp Leu Ile Met Ser Ser
                165                 170                 175
```

```
Leu Met Leu Leu Phe Leu Phe Thr Tyr Ile Tyr Leu Gly Glu Val Leu
            180             185             190
Lys Thr Tyr Asn Val Ala Met Asp Tyr Pro Thr Leu Leu Leu Thr Val
        195             200             205
Trp Asn Phe Gly Ala Val Gly Met Val Cys Ile His Trp Lys Gly Pro
    210             215             220
Leu Val Leu Gln Gln Ala Tyr Leu Ile Met Ile Ser Ala Leu Met Ala
225             230             235             240
Leu Val Phe Ile Lys Tyr Leu Pro Glu Trp Ser Ala Trp Val Ile Leu
                245             250             255
Gly Ala Ile Ser Val Tyr Asp Leu Val Ala Val Leu Cys Pro Lys Gly
            260             265             270
Pro Leu Arg Met Leu Val Glu Thr Ala Gln Glu Arg Asn Glu Pro Phe
        275             280             285
Pro Ala Leu Ile Tyr Ser Ser Ala Met Val Trp Thr Val Gly Met Ala
    290             295             300
Lys Leu Asp Pro Ser Ser Gln Gly Ala Leu Gln Leu Pro Tyr Asp Pro
305             310             315             320
Glu Met Glu Glu Asp Ser Tyr Asp Ser Phe Gly Glu Pro Ser Tyr Pro
                325             330             335
Glu Val Phe Glu Pro Pro Leu Thr Gly Tyr Pro Gly Glu Glu Leu Glu
            340             345             350
Glu Glu Glu Glu Arg Gly Val Lys Leu Gly Leu Gly Asp Phe Ile Phe
        355             360             365
Tyr Ser Val Leu Val Gly Lys Ala Ala Ala Thr Gly Ser Gly Asp Trp
    370             375             380
Asn Thr Thr Leu Ala Cys Phe Val Ala Ile Leu Ile Gly Leu Cys Leu
385             390             395             400
Thr Leu Leu Leu Ala Val Phe Lys Lys Ala Leu Pro Ala Leu Pro
                405             410             415
Ile Ser Ile Thr Phe Gly Leu Ile Phe Tyr Phe Ser Thr Asp Asn Leu
            420             425             430
Val Arg Pro Phe Met Asp Thr Leu Ala Ser His Gln Leu Tyr Ile
        435             440             445
```